US006106824A

United States Patent [19]
Kaplitt et al.

[11] Patent Number: 6,106,824
[45] Date of Patent: Aug. 22, 2000

[54] EXPRESSION OF GROWTH ASSOCIATED PROTEIN B-50/GAP-43 IN VITRO AND IN VIVO

[75] Inventors: Michael G. Kaplitt, New York, N.Y.; Joost Verhaagen, Utrecht, Netherlands

[73] Assignees: The Rockefeller University, New York, N.Y.; Rudolf Magnus Institute, Netherlands

[21] Appl. No.: 08/691,558

[22] Filed: Aug. 2, 1996

Related U.S. Application Data

[63] Continuation of application No. 08/106,209, Aug. 13, 1993, abandoned.

[51] Int. Cl.$^7$ .......................... A61K 48/00; C12N 15/12; C12N 15/86
[52] U.S. Cl. ................. 424/93.2; 435/172.3; 435/320.1; 514/44
[58] Field of Search ............................. 435/320.1, 172.3; 424/93.2; 514/44

[56] References Cited

U.S. PATENT DOCUMENTS 4,546,082  10/1985  Kurjan et al. ........................ 435/172.3

FOREIGN PATENT DOCUMENTS 2012311  3/1990  Canada .

OTHER PUBLICATIONS

Adames et al., "The c–myc oncogene driven by immunoglobul in enhancers induces lymphoid malignancy in transgenic mice", 1985, Nature 318:533–538.

Alexander et al., "Expression of the c–myc Oncogene under Control of an Immunoglobulin Enhnacer in E$\mu$–myc Transgenic Mice", 1987, Mol. Cell. Biol. 7:1436–1444.

Basi et al., "Primary Structure and Transcriptional Regulation of GAP–43, a Protein Associated with Nerve Growth", 1987, Cell 49:785–791.

Benowitz et al., 1981, "Specific Changes in Rapidly Transported Proteins During Regeneration of The Goldfish Optic Nerve", J. Neurosci. 1:300–307.

Benoist and Chambon, "In vivo sequence requirements of the SV40 early promoter region", 1981, Nature 290:304–310.

Benton and Davis, "Screening $\lambda$gt Recombinant Clones by Hybridization to Single Plaques in situ", 1977, Science 196:180.

Brinster et al., "Regulation of metallothionein–thymidine kinase fusion plasmids injected into mouse eggs", 1982, Nature 296:39–42.

Brown et al., "Motoneuron Sprouting Is Not Associated With Increases In GAP–43 MRNA", 1992, Soc. Neurosci. Abstract 18:605.

Burry et al., "Silver Enhancement of Gold Antibody Probes in Pre–embedding Electron Microscopic Immunocytochemistry", 1992, J. Histochem. Cytochem. vol. 40, No. 12:1849–1856.

Caceras et al., "Suppression of MAP2 in Cultured Cerebeller Macroneurons Inhibits Minor Neurite Formation", 1992, Neuron. 9:607–618.

Cimler et al. "Characterization of Murine cDNAs Encoding P–57, a Neural–specific Calmodul in–binding Protein", 1987, J. Biol. Chem. 262:12158–12263.

De Graan et al., "Phosphoprotein B–50 In Nerve Growth Cones From Fetal Rat Brain", 1985, Neurosci. Lett. 61:235–241.

De Koning et al., "Methods for Producing a Reproducible Crush in the Sciatic and Tibial Nerve of the Rat and Rapid and Precise Testing of Return of Sensory Function Beneficial of Melancortins", 1986, J. Neuro. Sci. 74:237–246.

De Koning et al., "Evaluation of cis–Diammimedichloroplatinum (II) (Cisplatin) Neurotoxicity in Rats", 1987, Toxicol. Appl. Pharmacol. 89:81–87.

Doster et al., "Expression of the Growth–Associated Protein GAP–43 in Adult Rat Retinal Ganglion Cells following Axon Injury", 1991, Neuron 6:635–647.

Easter et al., "Initial Tract Formation in the Mouse Brain", 1993, J. Neurosci. 13:285–299.

Felgner, et al., 1987, Proc. Natl. Acad. Sci. U.S.A. 84:7413–7417.

Felgner and Ringold, "Catonic Liposome–mediated transfection", 1989, Nature 337:387–388.

Glover, D.M. (ed.), 1985, DNA Cloning: A Practical Approach, MRL .

Goslin et al., "Development of neuronal polarity:GAP–43 distinguishes axonal from dendritic growth cones", 1988, Nature 336:672–674.

(List continued on next page.)

*Primary Examiner*—Johnny F. Railey, II
*Attorney, Agent, or Firm*—Klauber & Jackson

[57] ABSTRACT

The present invention relates to a viral vector capable of the transfer and in vivo expression of growth-associated protein (B-50/GAP-43) in neuronal target cells of a mammalian host. The viral vector contains a recombinant DNA molecule comprising a B-50/GAP-43 gene operably associated with a promoter, which promoter controls short term, high level expression of the B-50/GAP-43 gene. Preferably, the viral vector is a defective viral vector, in particular a defective herpes virus or an adeno-associated virus. In a specific embodiment, defective herpesvirus, adenovirus, and adeno-associated virus viral vectors containing the rat B-50/GAP-43 gene under control of the human cytomegalovirus immediate early promoter have been prepared. The invention further provides a method for treating nerve damage in a subject. The method comprises introducing a vector comprising a B-50/GAP-43 gene operably associated with a promoter into a damaged nerve tissue of a subject. Preferably, the promoter controls short term, high level expression of the B-50/GAP-43 gene, such that the B-50/GAP-43 gene is expressed in the tissue of the subject. Preferably, the vector used in the therapeutic methods of the invention is a viral vector. The vectors of the invention, capable of expression a B-50/GAP-43 gene, can also be used in vitro to enhance the survival of cultured cells, in particular, cultured neurons for transplantation.

9 Claims, 11 Drawing Sheets

OTHER PUBLICATIONS

Grosschedl et al., "Induction of a μ Immunoglobulin Gene into the Mouse Gene LIne: Specific Expression in Lymphoid Cells and Synthesis of Functional Antibody", 1984, Cell 38:647–658.

Grunstein and Hogness, "Colony hybridization: A method for the isolation of cloned DNAs that contain a specific gene", 1975, Proc. Natl. Acad. Sci. U.S.A. 72:3961.

Hammer et al., "Diversity of Alpha–Fetoprotein Gene Expression in Mice Is Generated by a Combination of Separate Enhancer Elements", 1987, Science 235:53–58.

Hanahan, "Heritable formation of pancreatic β–cell tumours in transgenic mice expressing recombinant insulin/simian virus 40 oncogenes", 1985, Nature 315:115–122.

Higuchi, 1989, "Using PCR to Engineer DNA", in *PCR Technology: Principles and Applications for DNA Amplication*, H. Erlich, ed., Stockton Press, Chapter 6, pp. 61–70.

Hoffman, "Expression of GAP–43, a Rapidly Transported Growth–Associated Protein, and Class II Beta Tubulin, Slowly Transported Cytoskeletal Protein, Are Coordinated in Regenerating Neurons", 1989, J. Neurosci. 9:893–897.

Holt, et al., "Lipofection of cDNAs in the Embryonic Vertebrate Central Nervous System", 1990, Neuron 4:203–214.

Hutchinson et al., "A complete library of point substitution mutations in the glucocorticoid response element of mouse mammary tumor virus", 1986, Proc. Natl. Acad. Sci. U.S.A. 83:710.

Hutchinson C., et al., "Mutagensis at a Specific Position in a DNA Sequence", 1978, J. Biol. Chem. 253:6551.

Jap Tjoen San et al., "Inhibition of Nerve Growth Factor–Induced B–50/GAP–43 Expression by Antisense Oligomers Interferes with Neurite Outgrowth of PC12 Cells", 1992, Biochem. Biophys. Res. Comm. 187:839–846.

Kaplitt et al., 1991, Molec. Cell. Neurosci. 2:320–330.

Katz et al., "Nerve Growth Cones Isolated form Fetal Rat Brain III. Calcium–dependent Protein Phosphorylation", 1985, J. Neurosci. 5:1402–1411.

Kelsey et al., "Species— and tissue–specific expression of human $α_1$–antitrypsin in transgenic mice", 1987, Genes and Devel. 1:161–171.

Kollias et al., Regulated Expression of Human Aτ–, β–, and Hybrid τβ–Globin Genes in Transgenic Mice: Manipulation of the Development Expression Patterns, 1986, Cell 46:89–94.

Kristjansson et al., "Evidence That the Synaptic Phosphoprotein B–50 Is Localized Exclusively in Nerve Tissue", 1982, J. Neurochem. 39:371–378.

Krumlauf et al., "Developmental Regulation of α–Fetoprotein Genes in Transgenic Mice", 1985, Mol. Cell. Biol. 5:1639–1648.

Kumagai et al., "Involvment of Growth–Associated Protein–43 with Irreversible Neurite Outgrowth by Dibutyryl Cyclic AMP and Phorbol Ester in NG108–15 Cells", 1992, J. Neurochem. 59:41–47.

Leder et al., "Consequences of Widespread Deregulation of the c–myc Gene in Transgenic Mice: Multiple Neoplasms and Normal Development", 1986, Cell 45:485–495.

Lewis et al., "Organization of microtubules in dendrites and axons is determined by a short hydrophobic zipper in microtubule–associated proteins MAP2 and tau", 1989, Nature 342:498–505.

Lewis and Bridgman, "Nerve Growth Cone Lamellipodia Contain Two Populations of Actin Filaments That Differ in Organiztion and Polarity", 1992, J. Cell Biol. 119:1219–1243.

Macagno, Eds.; Coggins and Zwiers, "B–50 (GAP–43): Biochemistry and Functional Neurochemistry of a Neuron–Specific Phosphoprotein", 1991, J. Neurochem. 56:1095–1106.

MacDonald, 1987, Hepatology 7:425–515.

Mackey, et al., 1988, Proc. Natl. Acad. Sci. U.S.A. 85:8027–8031.

Mason et al., "The Hypogonadal Mouse: Reproductive Function Restored by Gene Therapy", 1986, Science 234:1372–1378.

Miller et al., "Rapid Induction of the Major Embryonic α–Tubulin mRNA, Tα1, During Nerve Regeneration in Adult Rats", 1989, J. Neurosci. 9:1452–1463.

Mogram et al., "Development regulation of a cloned adult β–globin gene in transgenic mice", 1985, Nature 315:338–340.

Morton and Buss, "Accelerated Differentiation in Response to Retinoic Acid After Retrovirally Mediated Gene Transfer of GAP–43 into Mouse Neuroblastoma Cells", 1993, Eur. J. Neurosci. 4:910–916.

Nielander et al., "Primary Structure of the Neuron–Specific Phosphoprotein B–50 Is Identical To Growth–Associated Protein GAP–43", 1987, Neurosci. Res. Comm. 1:163–172.

Oestreicher et al., "Affinity–Purified Anti–B–50 Protein Antibody: Interference with the Function of the Phosphoprotein B–50 in Synaptic Plasma Membranes", 1983, J. Neurochem. 41:331–340.

Oliphant et al., "Cloning of random–sequence oligodeoxynucleotides", 1986, Gene 44:177.

Ornitz et al., "Elastase I Promoter Directs Expression of Human Growth Hormone and SV40 T Antigen Genes to Pancreatic Acinar Cells in Transgenic Mice", 1986, Cold Spring Harbor Symp. Quant. Biol. 50:399–409.

Pinkert et al., "An albumin enhancer located 10kb upstream functions along with its promoter to direct efficient, liver—specific expression in transgenic mice", 1987, Genes and Devel. 1:268–276.

Plantinga et al., "The expression of B–50/GAP–43 in Schwann cells in upregulated in degenerating peripheral nerve stumps following nerve injury", 1993, Brain Res. 602:69–76.

Readhead et al., "Expression of a Myelin Basic Protein Gene in Transgenic Shiverer Mice: Correction of the Dysmyelinating Phenotype", 1987, Cell 48:703–712.

Rosenthal et al., "Primary structure and mRNA localization of protein F1, a growth—related protein kinase C substrate associated with synaptic plasticity", 1987, EMBO J. 6:3611–6346.

Sambrook et al., 1989, "Molecular cloning: A laboratory manual," Second Edition, Cold Spring Harbor Laboratory Press.

Samulski et al., "A Recombinant Plasmid from Which an Infectiouis Adeno—Associated Virus Genome Can be Excised In Vitro and Its Use To Study Viral Replication", 1987, J. Virol. 61:3096–3101.

Samulski et al., "Helper—Free Stocks of Recombinant Adeno—Associated Viruses: Normal Integration Does Not Require Viral Gene Expression", 1989, J. Virol. 63:3822–3828.

Shani, M., "Tissue—specific expression of rat myosin light-chain 2 gene in transgenic mice", 1985, Nature 314:283–286.

Scharfmann et al., 1991, Proc. Natl. Acad. Sci. U.S.A. 88:4626–4630.

Shea et al., "Phospholipid—mediated Delivery of Anti–GAP–43 Antibodies into Neuroblastoma Cells Prevents Neuritogensis", 1991, J. Neurosci. 11:1685–1690.

Shirao et al., "Cloning of drebrin A and induction of neurite–like processes in debrin–transfected cells", 1992, Neuro. Report 3:109–112.

Skene and Willard, "Axonally Transported Proteins Associated with Axon Growth in Rabbit Central and Peripheral Nervous Systems", 1981, J. Cell Biol. 89:96–103.

Skene and Willard, "Characteristics of Growth–Associated Polypeptides in Regenerating Toad Retinal Ganglion Cell Axons", 1981, J. Neurosci. 1:419–426.

Skene etal., "A Protein Induced During Nerve Growth (GAP–43) Is a Major Component of Growth–Cone Membranes", 1986, Science 233:783–786.

Spaete R.R. et al., 1992, "The Herpes Simplex Virus Amplicon: A New Eucaryotic Defective–Virus Cloning–Amplifying Vector", In "The nerve growth cone," 1982, Cell 30:295–304.

"DNA Cloning: A Practical Approach," vol. I and II (D.N. Glover ed. 1985).

Stratford–Perricaudet et al. "Widespread Long–term Gene Transfer to Mouse Skeletal Muscles and Heart", 1992, J. Clin. Invest. 90:626–630.

Swift et al., "Tissue–Specific Expression of the Rat Pancreatic Elastase I Gene in Trnasgenic Mice", 1984, Cell 38:639–646.

Tetzlaff and Bisby, 1990, Rest. Neurol. Neuosci. 1:189–196.

Tetzlaff et al., "Response of Facial and Rubrospinal Neurone to Axontomy: Changes in mRNA Expression for Cytoskeletal Proteins and GAP–43", 1991, J. Neurosci. 11:2528–2544.

Towbin et al., "Electrophoretic transfer of proteins from polyacrylamide gels to nitrocellulose sheets Procedure and some applications", 1981, Proc. Natl. Acad. Sci. U.S.A. 76:4354–4356.

Van der Zee et al., "Expression of Growth–Associated Protein B–50 (GAP43) in Dorsal Root Ganglia and Sciatic Nerve During Rengerative Sprouting", 1989, J. Neurosci. 9:3505–3512.

Van Hooff et al., "Nerve Growth Factor–induced Changes in the Intracellular Localization of the Protein Kinase C Substrate B–50 in Pheochromocytoma PC12 Cells", 1989, J. Cell Biol. 108:1115–1125.

Verhaagen et al., "Early effect of an $ACTH_{4-9}$ analog (Org. 2766) on regenerative sprouting demonstrated by the use of neurofilament–binding antibodies isolated from a serum raised by α–MSH immunization", 1987, Brain Res. 404:142–150.

Verhaagen et al., "Elevated Expression of B–50 (GAP–43)–mRNA in a Subpopulation of Olfactory Bulb Mitral Cells Following Axotomy", 1993, J. Neurosci. Res. 35:162–169.

Verhaagen et al., "Light and Electron–Microscopical Study of Phosphoprotein B–50 Following Denervation and Reinnervation of the Rat Soleus Muscle", 1988, J. Neurosci. 8:1759–1766.

Verhaagen et al., "The Kinase C Substrate Protein B–50 and Axonal Regeneration", 1986, Brain Res. Bull. 17:737–741.

Wagner et al., "Nucleotide sequence of the thymidine kinase gene of herpes simplex virus type 1", 1981, Proc. Natl. Acad. Sci. U.S.A. 78:1441–1445.

Widmer and Caroni, "Phosphorylation–Site Mutagenesis of the Growth–associated Protein GAP–43 Modulates Its Effects on Cell Spreading and Morphology", 1993, J. Cell Biol. 120:503–512.

Wu et al., "Hepatocyte–directed Gene Transfer in Vivo Leads to Transient Improvement of Hypercholesterolemia in Low Density Lipoprotein Receptor–deficient Rabbits", 1992, J. Biol. Chem. 267:963–967.

Wu and Wu, "Receptor–mediated Gene Delivery and Expression In Vitro", 1988, J. Biol. Chem. 263:14621–14624.

Yankner et al., "Transfection of PC12 cells with the human GAP–43 gene: effects on neurite outgrowth and regeneration", 1990, Mol. Brain Res. 7:39–44.

Yamamoto, et al., "Identifiction of a Functional Promoter in the Long Terminal Repeat of Rous Sarcoma Virus", 1980, Cell 22:787–797.

Zoller and Smith, "Oligonucleotide–Directed Mutagenesis: A Simple Method Using Two Oligonucleotide Primers and a Single–Stranded DNA Template", 1984, DNA 3:479–488.

Zuber et al., "The Neuronal Growth–Associated Protein GAP–43 Induces Filopodia in Non–Neuronal Cells", 1989, Science 244:1193–1195.

Zwiers et al., "ACTH, Cyclic Nucleotides, and Brain Protein Phosphorylation In Vitro", 1978, Neurochem. Res. 1:669–677.

Zwiers et al., "Purification and Some Characteristics of an ACTH–Sensitive Protein Kinase and Its Substrate Protein in Rat Brain Membranes", 1980, J. Neurochem. 34:1689–1699.

Korsching et al., J. Neuroscience (1993) 13(7):2739–2748.

de Fiebre et al., Soc. Neurosci. Abstr. (1992) 18(1–2):781, abstract No. 331.2.

Bajocchi et al., Nature genetics (1993) 3:229–234.

Kalil., (1988) "Growth and Guidance of Axons in Two Pathways from the Mammalian Cerebral Cortex," In: *From Message to Mind*. S. S. Easter, Jr. et al. (eds.), Sinauer Associates, Inc.: Sunderland, MA.

Akli et al., Nature genetics (1993) 3:224–228.

Barinaga, Science (1994) 264:772–774.

Lowenstein, Bio/Technology (1994) 12:1075–1079.

Kaplitt et al., Nature Genetics (1994) 8:148–154.

Neve et al., Molecular Neurobiology (1991) 5:131–141.

Davidson et al., Nature genetics (1993) 3:219–223.

Le Gal La Salle et al., Science (1993) 259:988–990.

EXPRESSION OF GROWTH ASSOCIATED PROTEIN B-50/GAP-43 IN VITRO AND IN VIVO

This Application is a continuation of application Ser. No. 08/106,209 filed Aug. 13, 1993 now abandoned.

TECHNICAL FIELD OF THE INVENTION

The present invention relates to transgenic expression of the neuron growth associated protein B-50/GAP-43 introduced by a viral vector, and the vectors for transgenic expression. The invention further relates to treatment of diseases or disorders of the central or peripheral nervous system by with the transgenic vectors. In particular, the invention relates to treatment of nerve cell damage and induction of nerve regeneration.

BACKGROUND OF THE INVENTION

Adult nervous systems consist of complex neuronal networks. The initiation of nerve fiber formation is one of the first crucial events in an elaborate process eventually resulting in the establishment of these highly organized structures. The regulation of nerve fiber growth is under the control of extracellular molecules including growth factors, cell adhesion molecules and extracellular matrix components. In addition a number of proteins have been implicated in the intracellular mechanisms that regulate neurite outgrowth such as the cytoskeletal protein actin (Tetzlaff and Bisby, 1990, Rest. Neurol. Neurosci. 1:189–196; Lewis and Bridgman, 1992, J. Cell Biol. 119:1219–1227), juvenile forms of tubulin (Miller et al., 1989, J. Neurosci. 9:1452–1463; Easter et al., 1993, J. Neurosci. 13:285–299), microtubule associated proteins (Lewis et al., 1989, Nature 342:498–505; Caceras et al., 1992, Neuron. 9:607–618), the developmentally regulated dendritic protein Drebrin (Shirao et al., 1992, Neuro. Report 3:109–112) and the growth-associated protein B-50/GAP-43 (Skene, 1992, In "The nerve growth cone," Letourneau, Kater and Macagno, Eds.; Coggins and Zwiers, 1991, J. Neurochem. 56:1095–1106).

GAP-43 was originally discovered in an attempt to identify proteins specifically transported into growing axons (Skene and Willard, 1981, J. Cell Biol. 89:96–103; Skene and Willard, 1981, J. Neurosci. 1:419–426; Benowitz et al., 1981, J. Neurosci. 1:300–307). Earlier, a substrate of protein kinase C was isolated which was specific to nervous tissue and this protein was called B-50 (Zwiers et al., 1978, Neurochem. Res. 1:669–677; Zwiers et al., 1980, J. Neurochem. 34:1689–1699; Kristansson et al., 1982, J. Neurochem. 39:371–378). Subsequently, molecular cloning revealed that GAP-43 (Basi et al., 1987, Cell 49:785–791) and B-50 (Nielander et al., 1987, Neurosci. Res. Comm. 1:163–172) are the same protein and are also homologous to F1 (Rosenthal et al., 1987, EMBO J. 6:3611–6346), a calmodulin-binding protein (Cimler et al. 1987, J. Biol. Chem. 262:12158–12263) protein associated with long term potentiation and neuromodulin. An intense interest developed in determining what role, if any, B-50/GAP-43 plays in the development and regeneration of nerve fibers.

Studies on the localization and the regulation of B-50/GAP-43 protein expression and transport have yielded some insights in the role of this protein in axonal growth. The abundance of B-50/GAP-43 in growth cones (Katz et al., 1985, J. Neurosci. 5:1402–1411; De Graan et al., 1985, Neurosci. Lett. 61:235–241; Skene et al., 1986, Science 233:783–786) and developing embryonic neurons (Biffo et al., 1990), coupled with a down regulation of the expression of the protein shortly following target cell innervation, has furthered speculation that B-50/GAP-43 actively participates in the regulation of nerve fiber outgrowth (reviewed in Skene, 1992, supra). B-50/GAP-43 levels in injured PNS neurons are normally upregulated following a lesion and increased levels of B-50/GAP-43 are associated with periods of nerve regeneration (Skene and Willard 1981 (both citations), supra; Verhaagen et al., 1986, Brain Res. Bull. 17:737–741; Hoffman, 1989, J. Neurosci. 9:893–897; Van der Zee et al., 1989, J. Neurosci. 9:3505–3512). The decline in B-50/GAP-43 closely correlates with the completion of synapse formation and with the maturation of axon-glia interactions. This suggest that inhibitory signals associated with these events may play a role in down-regulating B-50/GAP-43 expression. Injury may interrupt this inhibitory influence, resulting in reinduction of B-50/GAP-43 expression (Skene, 1992, supra).

Despite the close correlation between B-50/GAP-43 expression and axonal growth, the precise role of this protein remains elusive. B-50/GAP-43 expression in cultured hippocampal neurons precedes the determination of neuronal polarity (Van Lookeren-Campagne et al., 1992). During the initial stages of nerve fiber elongation, B-50/GAP-43 is equally distributed in all short processes and their growth cones. As polarity in these cultured neurons develops, B-50/GAP-43 becomes more abundant in the faster growing axonal process (Goslin et al., 1988, Nature 336:672–674; Van Lookeren-Campagne et al., 1992, supra). In PC-12 cells treatment with nerve growth factor (NGF) results in a redistribution of B-50/GAP-43 from vesicular structures in the cytosol to the plasma membrane (Van Hooff et al., 1989, J. Cell Biol. 108:1115–1125). This redistribution occurs coincident with the initiation of nerve fiber outgrowth.

Some of the most direct, if undramatic, evidence supporting a role for B-50/GAP-43 in the determination of process outgrowth and cell shape has been obtained in experiments in which the levels of B-50/GAP-43 were manipulated in cell lines. Non-neuronal cells that express B-50/GAP-43 exhibit transient cell surface reactions during the first hours following plating of the cells (Zuber et al., 1989, Science 244:1193–1195; Widmer and Caroni, 1993, J. Cell Biol. 120:503–512). Stable transfection of neuroblastoma cell lines resulted in more rapid neurite outgrowth in response to differentiating stimuli (Yankner et al., 1990, Mol. Brain Res. 7:39–44; Morton and Buss, 1993, Eur. J. Neurosci. 4:910–916) and a longer maintenance of formed processes on withdrawal of such signals (Kumagai et al., 1992, J. Neurochem. 59:41–47). Down regulation of B-50 expression with anti-sense B-50 oligonucleotides or blocking of B-50/GAP-43 with anti-B-50/GAP-43 antibodies results in a diminished outgrowth response in neuroblastoma cells (Shea et al., 1991, J. Neurosci. 11:1685–1690; Jap Tjoen San et al., 1992, Biochem. Biophys. Res. Comm. 187:839–846).

However, it is by no means clear that the B-50/GAP-43 protein has a direct or indirect role in nerve growth or regeneration. For example, collateral motoneuron sprouting of uninjured nerves in response to partial denervation is not associated with increases in GAP-43 mRNA (Brown et al., 1992, Soc. Neurosci. Abstracts 18:605). Burry et al. (ibid.) found that neurite outgrowth was independent of GAP-43 expression, and that NGF stimulation of both events proceeds via different pathways. Similarly, Verhaagen et al. (1993, J. Neurosci. Res. 35:162–169), found that although expression of B-50 mRNA was upregulated in about 40% of olfactory bulb mitral cells following lesioning by transection of the lateral olfactory tract (LOT), enhanced B-50 expression is not accompanied by regeneration of the severed LOT.

Platinga et al. (1993, Brain Res. 602:69–76) detected expression of mRNA for B-50 in non-neuronal Schwann cells following sciatic nerve crush without the morphological changes in the Schwann cells that are characteristic of nerve sprouting.

The citation or identification of any reference in this application shall not be construed as an admission that such reference is available as prior art to the present invention.

SUMMARY OF THE INVENTION

The present invention relates to a viral vector capable of the transfer and in vivo expression of growth-associated protein (B-50/GAP-43) in neuronal target cells of a mammalian host. The viral vector contains a recombinant DNA molecule comprising a B-50/GAP-43 gene operably associated with a promoter, which promoter controls short term, high level expression of the B-50/GAP-43 gene. Preferably, the viral vector is a defective viral vector, in particular a defective herpes virus or an adeno-associated virus. In a specific embodiment, the viral vector contains a rat B-50/GAP-43 gene.

According to the present invention, the promoter can be a strong viral promoter, such as the human cytomegalovirus immediate early promoter. Alternatively, the promoter can be an inducible promoter. In yet another embodiment, the promoter can be a promoter for a gene expressed endogenously by a neuron.

The invention further provides a method for treating nerve damage in a subject. The method comprises introducing a vector comprising a B-50/GAP-43 gene operably associated with a promoter into a damaged nerve tissue of a subject. Preferably, the promoter controls short term, high level expression of the B-50/GAP-43 gene, such that the B-50/GAP-43 gene is expressed in the tissue of the subject. Preferably, the vector used in the therapeutic methods of the invention is a viral vector, as described above.

Accordingly, the invention provides for the treatment of nerve damage that results from a lesion, such as surgery, trauma, neurotoxin exposure, stroke, and the like. The invention also provides therapy for nerve damage that results from a disease or dysfunction of the nerve system, such as Alzheimer's disease, amyotrophic lateral sclerosis, multiple sclerosis, and the like.

The invention further provides pharmaceutical compositions comprising a vector, which vector comprises a B-50/GAP-43 gene operably associated with a promoter, which promoter controls short term, high level expression of the B-50/GAP-43 gene, and a pharmaceutically acceptable carrier. Preferably, the vector for use in the pharmaceutical compositions of the invention is a viral vector.

The vectors of the invention, capable of expression a B-50/GAP-43 gene, can also be used in vitro to enhance the survival of cultured cells, in particular, cultured neurons for transplantation.

DETAILED DESCRIPTION OF THE INVENTION

Figure 1:
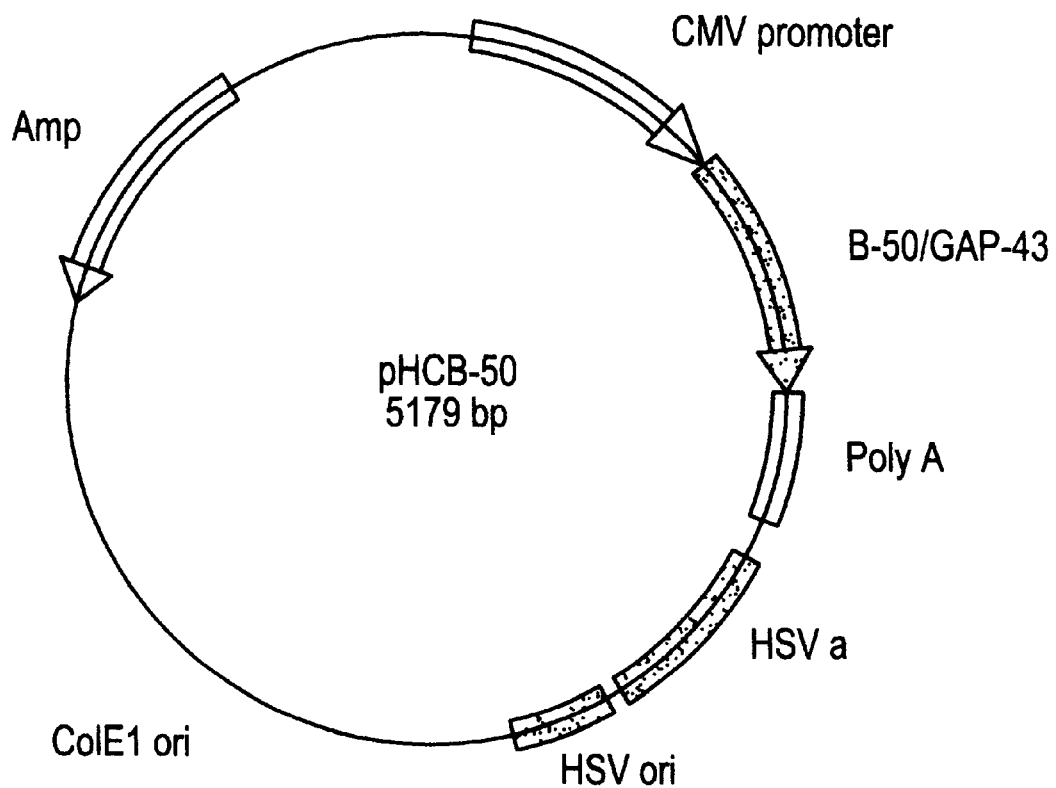
FIG. 1. Diagram of B-50/GAP-43 amplicon pHCB-50. pHCB-50 is based on amplicon pSRa-ori (Kaplitt et al., 1991, Molec. Cell. Neurosci. 2:320–330) and contains the B-50/GAP-43 coding sequence under the control of the CMV promoter. An SV40 polyadenylation signal (polyA) is located downstream of the transcription unit. The entire transcription unit was inserted in a unique Sal I restriction site in the polylinker of pSRa-ori. The position of the HSV cleavage packaging signal (HSV a), the HSV origin of replication (HSV ori), the ampicillin resistance gene (Amp) and the ColE1 ori are indicated.

In accordance with the present invention there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment. The term "vector" can also refer to a recombinant virus or defective virus containing a replicon to which another DNA segment may be attached. As used herein, the designation "p" in a name indicates a plasmid vector; the designation "v" indicates a viral vector; and the designation "dv" indicates a defective viral vector.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein, leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, EPO 0 116 201, publication date Jan. 12, 1983; U.S. patent application Ser. No. 522,909, filed Aug. 12, 1983). Further, the alpha-factor leader and its analogs have been found to secrete heterologous proteins from a variety of yeast, such as Saccharomyces and Kluyveromyces, (EPO 88312306.9 filed Dec. 23, 1988; U.S. patent application Ser. No. 139,682, filed Dec. 30, 1987, and EPO Publication No. 0 301 669, publication date Feb. 1, 1989).

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In its primary aspect, the present invention concerns introduction and expression of a vector containing the gene encoding growth-associated protein (B-50/GAP-43) in neural tissue of the central nervous system (CNS), such as the brain and the spinal cord, and neural tissue of the peripheral nervous system (PNS). B-50/GAP-43 associates with the cytoplasmic side of the neuronal plasma membrane through thio-ester bonds between fatty acids and two N-terminally located cysteine residues. Thus, expression of B-50/GAP-43 provides an intracellular stimulus regeneration or survival in vitro.

Expression of the B-50/GAP-43 protein is indicated for nerve regeneration after nerve damage has occurred. In one embodiment, a vector of the invention containing a gene encoding the B-50/GAP-43 protein is introduced into neural tissue, wherein the B-50/GAP-43 gene is expressed to treat nerve damage resulting from a traumatic lesion, e.g., resulting from surgery, injury, or exposure to a toxin. In another embodiment, the nerve damage can result form a disease or dysfunction of the nervous system. Such diseases or dysfunctions include, but are not limited to, Alzheimer's disease, in which neuropathology is associated with amyloidosis; stroke, in which nerve damage results from the loss of blood flow; multiple sclerosis, in which nerve damage can result from the autoimmune response associated with demyelination; and amyotrophic lateral sclerosis (ALS, or Lou Gehrig's disease), in which motor neurons progressively degenerate.

In another embodiment, expression of B-50/GAP-43 in cells cultured in vitro can increase the survival time or probability of survival of such cells. Of particular interest in this regard are fetal neurons that are cultured in vitro prior to transplantation.

Genes Encoding B-50/GAP-43

As pointed out in the Background of the Invention section, supra, genes encoding B-50/GAP-43 has been isolated (see, e.g., Basi et al., 1987, Cell 49:785–791; and Nielander et al., 1987, Neurosci. Res. Comm. 1:163–172). In a specific embodiment, infra, the cDNA encoding rat B-50/GAP-43 described by Nielander et al., supra, was used. The present invention contemplates use of any mammalian gene encoding B-50/GAP-43, whether genomic DNA or cDNA, from, any source, particularly from a human cDNA or genomic library. Such a library can preferably be prepared from neurons expressing B-50/GAP-43 mRNA.

Methods for obtaining the B-50/GAP-43 gene are well known in the art, as described above (see, e.g., Sambrook et al., 1989, supra).

Any mammalian cell potentially can serve as the nucleic acid source for the molecular cloning of a B-50/GAP-43 gene. The nucleic acid sequences encoding B-50/GAP-43 can be isolated from human, porcine, bovine, feline, equine, as well as additional primate sources, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene. Preferably, for packaging in a viral vector, a cDNA clone is used.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired B-50/GAP-43 gene may be accomplished in a number of ways. For example, if an amount of a portion of a B-50/GAP-43 geneor its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, proteolytic activity, or antigenic properties as known for B-50/GAP-43. In a specific example, infra, and antiserum specific for B-50/GAP-43 is used to confirm expression of the gene in a Western assay and by immunohistochemistry.

A B-50/GAP-43 gene can also be identified by mRNA selection, i.e., by nucleic acid hybridization followed by in vitro translation. In this procedure, fragments are used to isolate complementary mRNAs by hybridization. Such DNA fragments may represent available, purified B-50/GAP-43 DNA of another species (e.g., rat). Immunoprecipitation analysis or functional assays (e.g., proteolytic activity) of the in vitro translation products of the isolated products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against B-50/GAP-43 protein. A radiolabelled B-50/GAP-43 cDNA can be synthesized using the selected mRNA (from the adsorbed polysomes) as a template. The radiolabelled mRNA or cDNA may then be used as a probe to identify the B-50/GAP-43 DNA fragments from among other genomic DNA fragments.

Alternatives to isolating the B-50/GAP-43 genomic DNA or cDNA include, but are not limited to, chemically synthesizing the gene sequence itself from a known sequence or making cDNA to the mRNA which encodes the B-50/GAP-43. For example, RNA for cDNA cloning of the B-50/GAP-43 gene can be isolated from cells which express B-50/GAP-43, such as neurons. Other methods are possible and within the scope of the invention.

The present invention also relates to vectors containing genes encoding analogs and derivatives of B-50/GAP-43 that have the same functional activity as B-50/GAP-43. The production and use of derivatives and analogs related to B-50/GAP-43 are within the scope of the present invention. In a specific embodiment, the derivative or analog is functionally active, i.e., capable of exhibiting one or more functional activities associated with a full-length, wild-type B-50/GAP-43 protein. As one example, such derivatives or analogs induce dramatic morphological changes on fibroblast cells in vitro.

In particular, B-50/GAP-43 derivatives can be made by altering encoding nucleic acid sequences by substitutions, additions or deletions that provide for functionally equivalent molecules. Preferably, derivatives are made that have enhanced or increased functional activity relative to the native B-50/GAP-43.

Due to the degeneracy of nucleotide coding sequences, other DNA sequences which encode substantially the same amino acid sequence as a B-50/GAP-43 gene may be used in the practice of the present invention. These include but are not limited to nucleotide sequences comprising all or portions of B-50/GAP-43 genes which are altered by the substitution of different codons that encode the same amino acid residue within the sequence, thus producing a silent change. Likewise, the B-50/GAP-43 derivatives of the invention include, but are not limited to, those containing, as a primary amino acid sequence, all or part of the amino acid sequence of a B-50/GAP-43 protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding B-50/GAP-43 derivatives and analogs of the invention can be produced by various methods known in the art. The manipulations which result in their production can occur at the gene or protein level. For example, the cloned B-50/GAP-43 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of B-50/GAP-43, care should be taken to ensure that the modified gene remains within the same translational reading frame as the B-50/GAP-43 gene, uninterrupted by translational stop signals, in the gene region where the desired activity is encoded.

Additionally, the B-50/GAP-43-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated B-50/GAP-43 gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TABS linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Vectors

According to the present invention, the vector for in vivo administration of the gene encoding B-50/GAP-43 can be introduced via any strategy.

In one embodiment, the gene encoding B-50/GAP-43 is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a particular locus, e.g., in the brain or spinal chord, can be specifically targeted with the vector. In a specific embodiment, a defective herpes virus 1 (HSV1) vector is used (Kaplitt et al., 1991, Molec. Cell. Neurosci. 2:320–330). In another specific embodiment, the viral vector is an attenuated adenovirus vector, such as the vector described by Stratford-Perricaudet et al. (1992, J. Clin. Invest. 90:626–630). In a preferred embodiment, the vector is a defective adeno-associted virus vector (Samulski et al., 1987, J. Virol. 61:3096–3101; Samulski et al., 1989, J. Virol. 63:3822–3828). Surprisingly, the adenovirus and adeno-associated virus vectors have been found to be effective in transfecting neurons. For example, as shown in a specific example, infra, the AAV vector can be used to express the lacZ gene in neurons.

An advantage of the AAV vector is that it can be purified from helper adenovirus quite readily, either by heating to 56° C., or by cesium gradient centrifugation. This ease in purification offers a significant advantage over defective HSV vectors, since the defective HSV vector must be replicated with helper HSV, so the two virions have the same coat and cannot be separated. Thus, mutant helper HSV is used, but will be administered with the defective HSV.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of the B-50/GAP-43 gene (Felgner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). Lipofection into the nervous system in vivo has recently been achieved (Holt, et. al., 1990, Neuron 4:203–214). The use of lipofection to introduce exogenous genes into the nervous system in vivo has certain practical advantages. Molecular targeting of liposomes to specific cells represents one area of benefit. It is clear that directing transfection to limited neuronal types would be particularly advantageous in a tissue with such cellular heterogeneity as the brain. Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. This is particularly the case where an axon has been cut, thus exposing the axonal cytoplasm. Any DNA in proximity to the cut axon may be taken up and transported via the well known axon transport mechanism to the cell body, where the plasmid may enter the nucleus. It is contemplated that plasmid DNA containing a gene encoding B-50/GAP-43 can be administered as first aid to a subject suspected of suffering nerve damage, especially where axotomy is suspected. Retrograde axonal transport of the vector may be enhanced by coupling the plasmid to an appropriate carrier, which normally undergoes retrograde, rather than antegrade, transport.

In another embodiment, the vector containing the gene encoding B-50/GAP-23 can be introduced via a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Vectors are introduced into the desired host cells in vitro by methods known in the art, e.g., transfection, electroporation, microinjection, transduction, cell fusion, DEAE dextran, calcium phosphate precipitation, lipofection (lysosome fusion), use of a gene gun, using a viral vector, with a DNA vector transporter, and the like.

Expression vectors containing B-50/GAP-43 gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a B-50/GAP-43 gene inserted in an expression vector can be detected by nucleic acid hybridization using probes comprising sequences that are homologous to an inserted B-50/GAP-43 gene. In the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In the fourth approach, recombinant expression vectors can be identified by assaying for the activity of the B-50/GAP-43 gene product expressed by the recombinant. Such assays can be based, for example, on the physical or functional properties of the B-50/GAP-43 gene product in in vitro assay systems, e.g., dramatic changes is cell morphology, as demonstrated in Example 1, infra.

The vectors of the invention can be prepared with a pharmaceutically acceptable carrier, as defined above, for administration to a subject.

Promoters

According to the present invention, the gene encoding B-50/GAP-43 can be under the control of any promoter. Preferably, for in vivo administration to effect neuron regeneration, the promoter provides for high level expression of B-50/GAP-43 for a finite period of time. Thus, the preferred promoters are promoters that are active for a short time, such as viral promoters for early genes. In a specific embodiment, infra, the human cytomegalovirus (CMV) immediate early promoter is used to effect transient expression of B-50/GAP-43. Alternatively, an inducible promoter can be used. However, the present invention contemplates use of any promoter to control expression of B-50/GAP-43. Selection of the promoter depends on the desired use, e.g., whether it is for neuron regeneration or to enhance the survival time of cells in vitro. For example, expression of B-50/GAP-43 may be controlled by any promoter/enhancer element known in the art, but these regulatory elements must be functional in the host or host cell selected for expression.

Promoters which may be used to control B-50/GAP-43 gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987; Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378). Alternatively, expression of the B-50/GAP-43 gene can be under control of an inducible promoter, such as metallothionein promoter, which is induced by exposure to heavy metals. Such a promoter is particularly attractive for PNS regeneration, since there is no need to overcome the blood-brain barrier under that circumstance. For control of the gene transfected into certain brain cells, a glucocorticoid inducible promoter can be used, since glucocorticoids can cross the blood-brain barrier. Alternatively, an estrogen inducible promoter, which would be active in the hypothalamus and other areas responsive to extrogen, can be used. The present invention contemplates the use of any promoter inducible by a pharmacologic agent that can cross the blood-brain barrier and influence transcription.

In Vitro and In Vivo Model Systems

A vector that contains a gene encoding B-50/GAP-43 can be tested according to the present invention in vitro or in vivo. For example, the vector can be used to transform neuronal or non-neuronal cells, in particular cells such as Vero and COS cells. The transformed cells will demonstrate changes in morphology. Preferably, these changes will be dramatic. For example, the cells may exhibit significant membrane ruffling and filopodial extensions. Preferably, for a highly effective vector, substantially all the cells in the culture exhibit these morphological changes. The cells may also express processes of significant length. In a specific embodiment, Vero cells may express processes of a mean length of 165 $\mu$m. Another hallmark of such in vitro culture systems is the timing of the morphological changes. Preferably, extensive changes occur gradually, and persist at least up to about 72 hours.

Nerve recovery can be demonstrated using animal models. In particular, the present invention contemplates a number of sources of neuropathy that can be treated with the vectors of the invention. These models include, but are not limited to, nerve crush and mechanical nerve trauma, including axonal transection; temporal occlusion of a blood vessel to mimic stroke; experimental allergic (or autoimmune) encephalomyelitis (EAE), a well studied rodent model of multiple sclerosis; and cisplatin. Nerve crush and cisplatin induced neuropathy have been used previously as animal models for the study of nerve recovery.

The well defined nerve tracts in the CNS constitute good systems to study the effectiveness of the vectors of the invention. The lateral olfactory tract is a relatively short (0.3 to 1 cm) myelinated fiber tract that guides the axons of the olfactory bulb mitral cells to groups of target neurons in the pyriform cortex, the amygdala and the hypothalamus. Nerve regeneration can be followed after axotomy (transection) of the lateral olfactory tract (Verhaagen et al., 1993, J. Neurosci. Res. 35:162–169). For example, one week following viral infusion in the olfactory bulb, the LOT can be transacted as described (Verhaagen et al., 1993, supra). formation of regenerating nerve fibers can be studied by immunohistochemistry for neurofilament (Verhaagen et al., 1987, Brain Res. 404:142–150). To ensure that ingrowing sprouts in central lesions are indeed derived from the damaged nerve cells and not from collateral ingrowth from other brain areas, the source of the sprout is established by retrograde tracing with fluorescent dy DiI.

The rubrospinal tract spans many centimeters in the spinal cord of the rat and is an important system in the coordination of locomotion. Transection of the rubrospinal tract can serve as a model for spinal cord trauma in humans. Methods for transecting nerve tracts and following nerve regeneration are well known in the art (see, e.g., Plantinga et al., 1993, Brain Res. 602:69–76; De Koning et al., 1986, J. Neuro. Sci. 74:237–246).

Reproducible mechanical nerve damage can be obtained by crushing the sciatic nerve with a wathcmakers forceps. Following a nerve crush, newly formed nerve fibers cross the crushed nerve area and eventually reinnervate their target cells in muscle and skin. The repair process can be followed in time using histological, electrophysiological and functional methods of investigation (see Verhaagen et al, 1987, supra; De Koning et al., 1986, J. Neurol. Sci. 74:237–246). Although reinnervation of most target cells occurs within 3 to 4 weeks following nerve crush, nerve fibers and their myelin sheaths remain thinner for up to one year following the lesion. Thus, the consequences of nerve damage remain detectable for an extended period of time. Introduction of a vector of the invention, preferably into the cell body of the crushed nerve, and preferably using a viral vector with expression of the B-50/GAP-43 gene under control of a high level, transient promoter, can accelerate the nerve repair process. The viral vector can be injected into the sciatic nerve one week prior to crush. Five days after crush the first newly formed sprouts penetrating the distal nerve stump are counted using an immunocytochemical detection method for neurofilament protein (Verhaagen eta I., 1987, supra), and functional recovery of the damaged nerve can be measured using the well established footflick or walking pattern tests (De Koning et al., 1986, supra).

Cisplatin is a neurotoxic agent with neurotoxic side effects. In an animal model, cisplatin induction of neuropathy and the effect of B-50/GAF-43 expression from a vector of the invention can be studied, similar to a study that has been used to evaluate the neurotrophic effects of neuropeptides (De Koning et al., 1987, Toxicol. Appl. Pharmacol. 89:81–87). In rats treated with cisplatin, a neuropathy develops and starts to become detectable in the fifth week of the treatment period as seen by decreased sensory nerve conduction velocity in sciatic nerve fibers. Expression of B-50/GAP-43 from a vector of the invention can accelerate the increase in the level of B-50/GAP-43 produced naturally by the damaged neurons. The ability of high levels of B-50/GAP-43 to protect neurons from cisplatin toxicity can be studied by administration of the vector of the invention one week prior to subjecting the animal to cisplatinum treatment. The development of the neuropathy can be followed by measuring the sensory nerve conduction velocity and the motor nerve conduction velocity (De Koning et al., 1987, supra).

It is readily appreciated by one of ordinary skill in the art that a number of control groups should be used in animal model studies. Such controls include animals that have been lesioned and treated with recombinant DNA or viral vectors that do not contain the B-50/GAP-43 gene. For example, if the treatment vector is dvHSVB-50, the control vector can be dvHSVlac.

In a further embodiment, vectors that coexpress B-50/GAP-43 and a nerve growth factor, such as NGF, or a nerve adhesion molecule, such as N-CAM, can be employed in the animal models.

Methods of Treatment

The present invention provides methods for the treatment of nerve damage associated with a lesion or a disease or dysfunction of the nervous system. Accordingly, the vector of the invention can be administered to a mammalian subject who has suffered nerve damage. Preferably the subject is a human, although the methods of the invention are contemplated for use in other mammalian species, including but not limited to domesticated animals (canine and feline); farm animals (bovine, ovine, equine, caprine, porcine, and the like); rodents; and undomesticated animals.

The B-50/GAP-43 expression vector of the invention can be employed for the effect of B-50/GAP-43 on the regenerative capacity of damaged neurons. Neurons of the adult mammalian central nervous system usually fail to regenerate following injury. Although B-50/GAP-43 is induced in some CNS nerve cells following lesion, such increases are relatively slow as compared to inductions in the PNS (Tetzlaff et al., 1991, J. Neurosci. 11:2528–2544; Verhaagen et al., 1993, J. Neurosci. Res. 35:162–169) and are only observed when axons are injured in close proximity to their cell bodies (Doster et al., 1991, Neuron 6:635–647). Although the present invention is not intended to be limited by any particular theory of operation, it was speculated that one of the factors that may contribute to the poor regeneration of injured central nervous system neurons may relate to the diminished capacity of these neurons to up regulate B-50/GAP-43. The expression, of B-50/GAP-43 via a defective viral vector in damaged central nervous system neurons can enhance their regenerative capacity.

The present invention contemplates introduction of a therapeutically effective amount of a vector for the treatment of nerve damage resulting from any lesion, such as surgery, trauma, exposure to a toxin, or the like. The invention further contemplates introduction of a therapeutically effective amount of a vector of the invention for the treatment of nerve damage associated with a disease or dysfunction of the nervous system such as but not limited to, Alzheimer's disease, stroke, amyloidosis, amyotrophic lateral sclerosis, multiple sclerosis, and the like. In a preferred aspect, a gene encoding B-50/GAP-43 is introduced via a defective viral vector, such as a defective HSV1 vector, or more preferably, a defective AAV vector. Such vectors provide for a high degree of transfection in a targeted area. Thus, the vector containing a gene encoding B-50/GAP-43 can be targeted specifically to the site of nerve damage by injecting the vector into the nerve tissue at the site of the nerve damage. The site of the nerve damage can be determined using imaging techniques that are known in the art, such as computer assisted tomography (CAT) scans and magnetic resonance imaging (MRI).

The vectors of the invention can be administered to enhance nerve regeneration in combination with other therapeutic approaches. Preferably, the therapeutic approach chosen involves external stimuli, thus complementing the internal stimulus effected by B-50/GAP-43 (which, as noted above, is a cytoplasmic protein associated with the plasma membrane). For example, the vector of the invention can be introduced to neural tissue undergoing treatment with nerve growth factor, brain-derived neurotrophic factor, ciliary neurotrophic factor, nerve adhesion molecules, such as N-CAM, and the like. These factors stimulate nerve growth, which can be enhanced with high level expression of B-50/GAP-43. Such nerve growth factors or adhesion molecules can conveniently be provided via co-expression of a gene encoding such factors from the vector of the invention containing B-50/GAP-43. Alternatively, introduction of a vector of the invention can accompany therapy to break down glial scars, for example, use of a glial cell toxic factor.

The present invention will be better understood from a review of the following illustrative description presenting the details of the constructs and procedures that were followed in its development and validation.

EXAMPLE 1

This Example describes the creation and application of a defective herpes simplex viral (HSV) vector for B-50/GAP-43, a neural growth-associated phosphoprotein. The example demonstrates abundant expression of B-50/GAP-43 in cultured non-neuronal cells via this HSV vector which contains a single B-50/GAP-43 transcription unit. When B-50/GAP-43 was expressed in non-neuronal cells major morphological changes occurred that included extensive membrane ruffling, the formation of filopodia and long thin extensions reminiscent of neurites. These extensions often terminated in growth cone-like structures. Quantitation of these morphological changes at different times following infection demonstrates that the surface area of the B-50/GAP-43 expressing cells started to increase between 6 and 10 hours post-infection. At 72 hours B-50/GAP-43 positive cells were 3.0 times larger in size and one third of the cells expressed long processes with a mean length of 165±14.5 $\mu$m. Ultrastructural studies of cells 48 hours after infection revealed that B-50/GAP-43 is predominantly localized at the plasma membrane. Some immunoreactivity was associated with vesicular structures that appear to be in-transit in the processes. These observations demonstrate that B-50/GAP-43 can induce a neuron-like morphology in non-neuronal cells persisting for several days in culture. The defective viral vector will enable gene transfer to express B-50/GAP-43 in neurons in vivo.

Materials and Methods

Construction of amplicons. The construction of amplicon pHCL containing the bacterial lacZ gene under the control of the human Cytomegalovirus immediate early (CMV) promoter has been described previously (Kaplitt, et al., 1991). The amplicon pHCB-50 (FIG. 1) was generated as follows: Sal I restriction sites were introduced 5'- and 3' of the CMV-promoter-SV-40 poly(A) signal expression cassette of pcDNA I (Invitrogen) using the polymerase chain reaction (PCR). The PCR product was digested with SalI, gel purified and ligated in the SalI site of pGEM2 (Promega) resulting in PGEM-CMV. An EagI and SmaI site were introduced 5'- and 3' of the rat B-50 coding sequence directly adjacent of the translation start and stop codons using the B-50 CDNA (Nielander et al. 1987) as a template. The PCR product was digested with EagI and SmaI and cloned in the EagI and EcoRV sites of pGEM-CMV resulting in pGEM-CMV-B-50. The B-50 coding sequence in pGEM-CMV-B50 was sequenced. This revealed no PCR errors or cloning artifacts. pGEM-CMV-B50 was digested with SalI and the CMV-B50-poly(A) fragment was cloned in pSRa-ori, a plasmid containing the HSV-1 cleavage/packaging signal and HSV-2 origin of replication (Kaplitt, et al., 1991, supra). This yielded amplicon pHCB-50 (FIG. 1).

Tissue culture and generation of defective viral vectors. Tissue culture media and reagents were from Gibco. Vero (African green monkey kidney cells) were obtained from the American Tissuetype Culture Collection and rabbit skin cells were obtained using standard techniques. These cell lines were maintained in Dulbecco's modified Earle's medium (DMEM) containing 10% inactivated fetal calf serum (IFCS) at 39° C. in an atmosphere of 5% $CO_2$. For the production of virus stocks, Vero cells were plated and allowed to grow to confluence in T150 tissue culture flasks (Nunc). Defective viral particles were generated as described previously (Kaplitt et al., 1991, supra) using a temperature sensitive mutant helper virus (tsK) obtained from J. Subak-Sharpe, Institute of Virology (Glasgow, Scotland). Defective viral titers were determined by histochemical staining for β-gal or by immunohistochemistry for B-50/GAP-43 as described below.

Infection of cells with defective viral vectors. To analyze the B-50/GAP-43 protein product synthesized via dvHCB-50 and to study the effect of B-50/GAP-43 on cellular morphology, cells were cultured at densities of $2\times10^4$ cells per $cm^2$ on poly-L-lysine (Sigma) coated microscope slides (26×40 mm) in DMEM with 10% IFCS. Cells were allowed to grow for 6 to 72 hours following plating and were infected with 15 µl of concentrated virus diluted in 1 ml phosphate buffered saline (PBS)/1% IFCS per microscope slide. One and a half hour later the virus containing buffer was removed, fresh DMEM/10% IFCS was added to the cells. The cells were allowed to grow for 6 to 72 hours at 39° C. and were subsequently processed for Western blotting or light- and electron microscopy.

Gel electrophoresis and immunoblotting. For Western blot analysis, B-50/GAP-43 infected Vero cells were removed from the microscope slide at 24 and 48 hours following infection using a denaturing electrophoresis sample buffer (Zwiers et al., 1976, Neurochem. Res. 1:669–677). Prior to electrophoresis, proteins in sample buffer were heated for 10 min. at 80° C. Proteins were separated by sodium dodecylsulfate (SDS) polyacrylamide gel electrophoresis (PAGE) (Zwiers et al., 1976, supra) and separated proteins were transferred from the 11% gels to nitrocellulose (Towbin et al., 1981, Proc. Natl. Acad. Sci. U.S.A. 76:4354–4356). Immunostaining of the blots with affinity purified anti-B-50/GAP-43 antibody derived from antiserum #8921 (Oestreicher et al., 1983, J. Neurochem. 41:331–340) was performed under standard conditions (Verhaagen et al., 1988, J. Neurosci. 8:1759–1766).

Light microscopy. Cells in twelve-well microtiter plates (for the determination of the titers of the viral stocks) or cells cultured on poly-L-lysine coated microscope slides (to study effects of B-50/GAP-43 on morphology) were fixed for 15 min. in 4% paraformaldehyde in 0.1M phosphate buffer (PB). Following fixation, cells were rinsed extensively with PBS. Beta-galactosidase expressing cells were visualized with a standard histochemical staining procedure using X-gal as a substrate (Sambrook et al., 1989, "Molecular cloning: A laboratory manual," Second Edition, Cold Spring Harbor Laboratory Press). B-50 was detected with affinity purified polyclonal rabbit antibodies (dilution 1:2500). All incubations with antibody were at room temperature in PBS containing 0.1% Triton X-100 and 0.2% BSA. After each incubation with antibody cells were washed with PBS/0.1% Triton X-100. Primary antibody incubations were performed overnight. Antigen-antibody binding was visualized with biotinylated second antibodies and an avidin/biotin/HRP staining kit (Vector laboratories, Burlingame, Calif.) according to the procedure supplied with the kit. Immunostained cells were briefly counterstained with hematoxylin, dehydrated, embedded in Depex mounting medium and examined in an Olympus BH-2 microscope.

Quantification of cell shape. For each cell the surface area, the number of cellular extensions and the length of the extensions were determined with a computerized image analysis system (DIFA, Breda, The Netherlands). To this end cells were visualized on a television screen with a 20× objective using an Olympus BH-2 microscope equipped with a video camera linked to an IBM computer. To avoid biased sampling three randomly chosen fields were marked with a pencil on each slide by an investigator not directly involved in the quantification and all cells present in these field were analyzed. Thirty to 59 β-Gal and B-50/GAP-43 cells were analyzed at 6, 10, 24, 48 and 72 hours post-infection.

Electron microscopy. Vero cells cultured on poly-L-lysine coated thermanox coverslips were fixed in 4% paraformaldehyde/2% glutaraldehyde (biological grade, Polysciences, Warrington, U.S.A.) in PB for 20 min at 4° C. Fixed cells were washed in PB and aldehyde groups were inactivated in a freshly prepared solution of sodium borohydride and 0.1% glycine in PB. Before and after each immuno-incubation cells were rinsed for 1 hour in 0.5% BSA and 0.1% gelatin in PB. This solution was also used as diluent of the primary and secondary antibodies. The incubation solution of the primary antibody also contained 0.1% saponin and 2% normal goat serum. Cells were incubated overnight in 1:300 diluted affinity purified anti-B-50/GAP-43 antibodies. The next morning cells were rinsed for 2 hours and incubated in 1:80 diluted goat anti-rabbit immunoglobulins conjugated to 1 nm gold particles (Aurion, Wageningen, NL) for 5 hours at 37° C. The cells were subsequently rinsed for 1 hour in 0.5% BSA and 0.1% gelatin in PB and in PB, fixed for 10 minutes in 2.5% glutaraldehyde in PB, washed in PB and incubated in 0.1% osmium tetroxide in PB for 30 min. After 3 rinses of 3 minutes each in deionized water the cells were treated according the N-propylgallate silver enhancement method (Burry et al., 1992, J. Histochem. Cytochem.). Thereafter Vero cells were rinsed in deionized water and stored temporarily in PB. Subsequently cells were rinsed 3 times in deionized water, fixed in 2% uranyl acetate in 50% ethanol for 30 minutes and dehydrated in a series of graded ethanols. After rinsing in 100% propylene oxide, the cells were embedded in epon. Thermanox coverslips were removed from the resin, leaving the cells at the surface of the epon block. Ultrathin sections of the epon embedded cells were prepared with a Reichert-Jung ultracut microtome, mounted on formfar-coated nickel grids. The gold particles were silver enhanced and cells were photographed without counter staining in a Philips CM10 electron microscope.

Results

Creation of B-50/GAP-43 amplicons and generation of defective viral vector. Amplicon pHCB-50 is based on a previously described prototype, pSRa-ori (Kaplitt et al., 1991, Molec. Cell. Neurosci. 2:320–330). This plasmid contains the HSV cleavage packaging signal ("a" sequence) and the origin of replication (ori). The B-50/GAP-43 coding region was placed under the control of the CMV promoter with the SV40 poly-adenylation signal downstream of the coding region. This transcription unit was inserted into pSRa-ori creating pHCB-50 (FIG. 1). Following transfection of the amplicons (PHCL and pHCB-50) into rabbit skin cells, defective HSV vectors were created by superinfection with the temperature-sensitive helper virus tsK. The resulting viral stocks were serially passaged and the helper and defective titers were determined for each passage as described in the materials and methods section. Immunohistochemistry was used to detect expression of B-50/GAP-43 protein 24 hours following infection. Positive cells were clearly identified in plates infected with dilutions of the viral vector dvHCB-50. Uninfected cells, as well as cells infected with helper virus alone or with the lacZ-expressing virus dvHCL were completely negative for B-50/GAP-43. In addition, the number of B-50/GAP-43 positive cells changed proportionately to the viral dilution factor, thereby confirming that the positive cells were the result of a viral infection. This demonstrates that B-50/GAP-43 protein expression was the result of expression from defective viral vector dvHCB-50.

Figure 2:
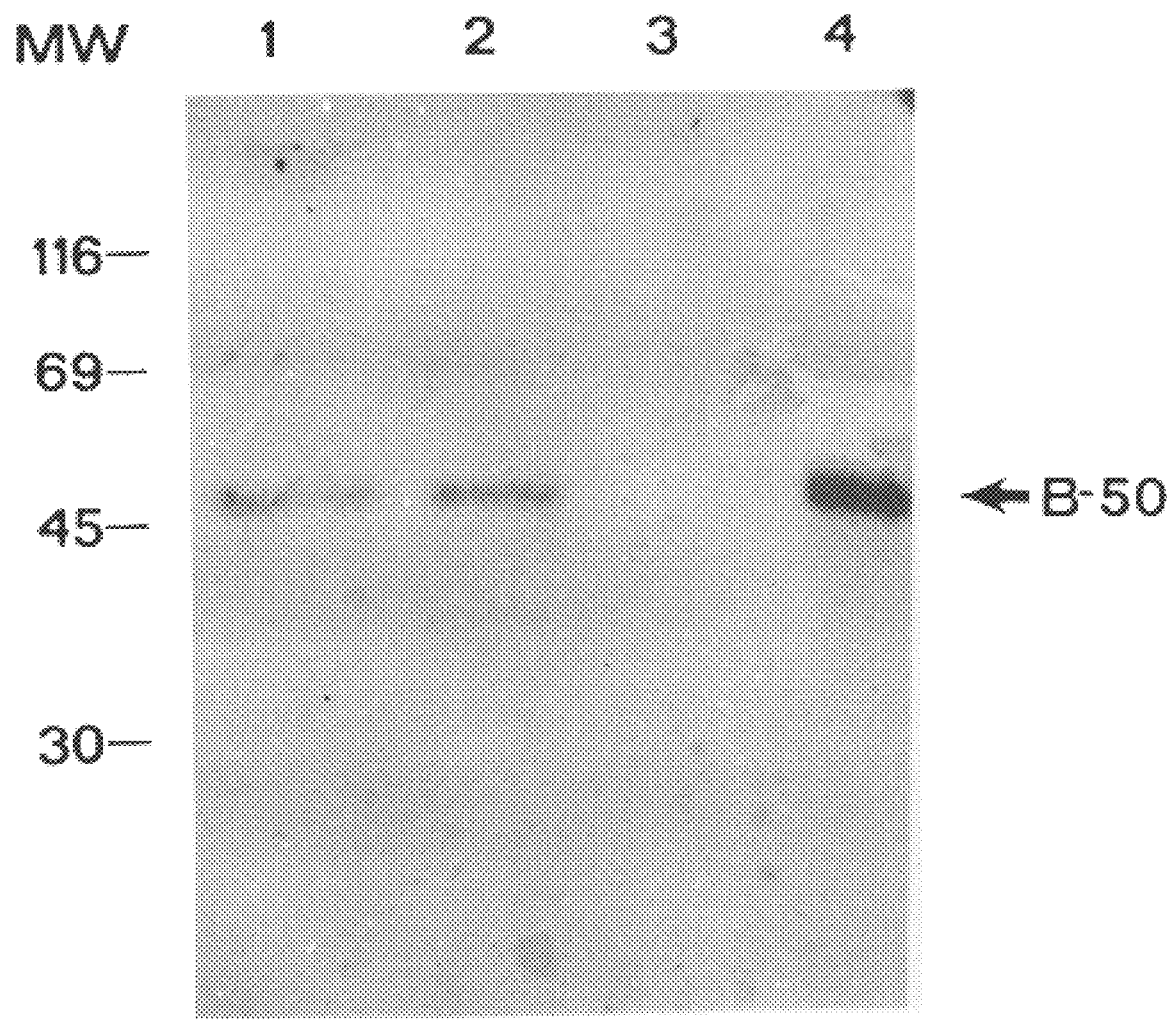
FIG. 2. Analysis of B-50/GAP-43 protein expression from dvHC-B-50. A Western blot prepared from Vero cell proteins extracted 24 (lane 1) and 48 (lane 2) hours after infection with dvHC-B-50 and proteins from non-infected Vero cells (lane 3) and from mouse brain (lane 3) was incubated with anti-B-50/GAP-43 antibody. The B-50/GAP-43 immunoband in dvHCB-50 infected Vero cell extracts runs at the same position as B-50/GAP-43 in a protein extract from mouse brain. This demonstrates that the expression of B-50/GAP-43 in Vero cells via dvHCB-50 results in the synthesis of intact B-50/GAP-43. The position of molecular weigh markers is indicated on the left.

To determine if infection of Vero cells results in the expression of intact B-50/GAP-43, a Western blot with proteins extracted from dvHCB-50 infected Vero cells, non-infected Vero cells and mouse brain was incubated with B-50/GAP-43 antibody. Expression of B-50/GAP-43 is readily detectable in infected Vero cells but is absent from non-infected cells. B-50/GAP-43 expressed in Vero cells via dvHCB-50 migrates at the same position as B-50/GAP-43 from mouse brain (FIG. 2).

Figure 3A:
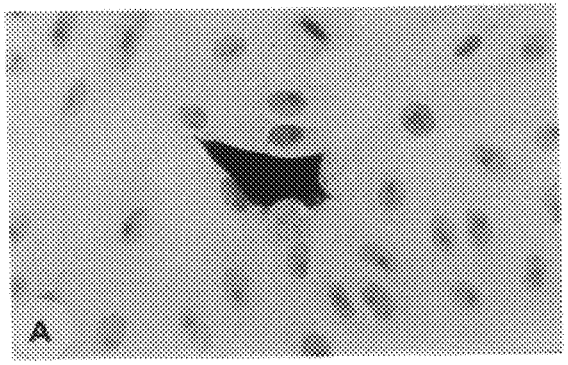
FIG. 3 (Panels A–G). Comparison of the morphology of Vero cells infected with dvHCL and dvHCB-50. At various time points following infection with defective viral vectors, cells were fixed and β-gal or B-50/GAP-43 expression was visualized with a histochemical staining (β-gal) or by immunohistochemistry (B-50/GAP-43), respectively. (A,B) Vero cells expressing β-gal 48 hours after infection with dvHCL. (C,D,E,F,G) Vero cells expressing B-50/GAP-43 48 hours (C,E,F,G) and 72 hours (D) after infection with dvHCB-50. B-50/GAP-43 expression result. in enlarged cells with ruffled membranes and numerous filopodia (C) or in cells with long thin processes (D,E,F). Details of Vero cells in F and G illustrate growth cone-like structures on B-50/GAP-43 expressing cells. (G) is a magnification of the process in (E). Changes such as shown here were observed in nearly all cells expressing B-50/GAP-43 between 24 and 72 hours following infection in 4 independent experiments. In contrast no such changes were seen in cells expressing B-50/GAP-43 at 6 hours post-infection or in β-gal expressing cells. The scale bar is 50 μm (for A,C,D,E) and 19 μm for (B,F,G).
Figure 3B:
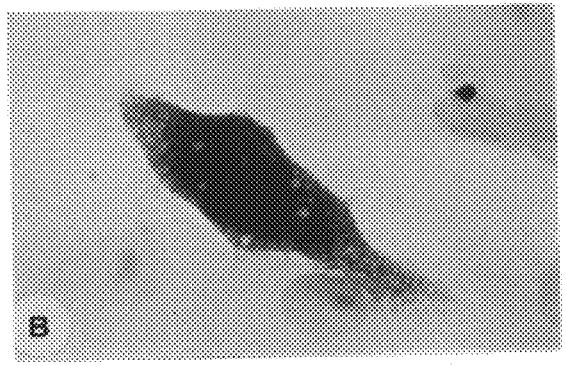
Figure 3C:
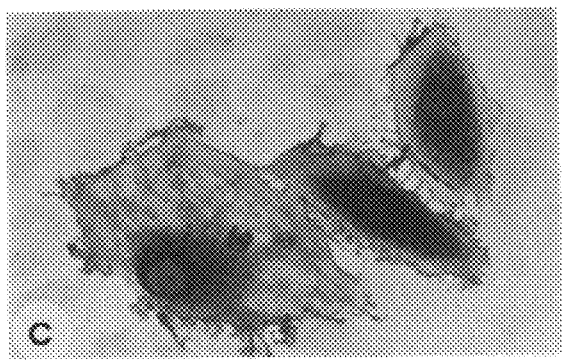
Figure 3D:
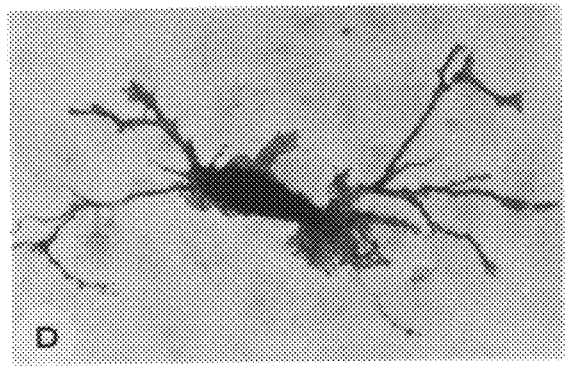
Figure 3F:
Figure 3E:
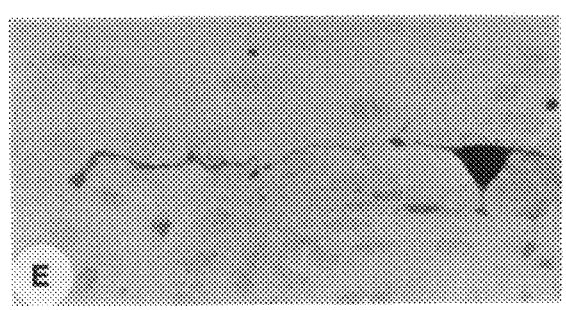
Figure 3G:
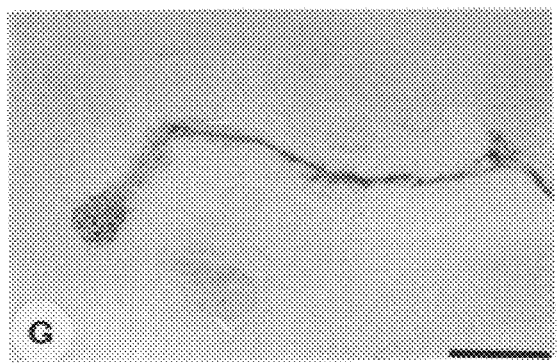
Figure 4:
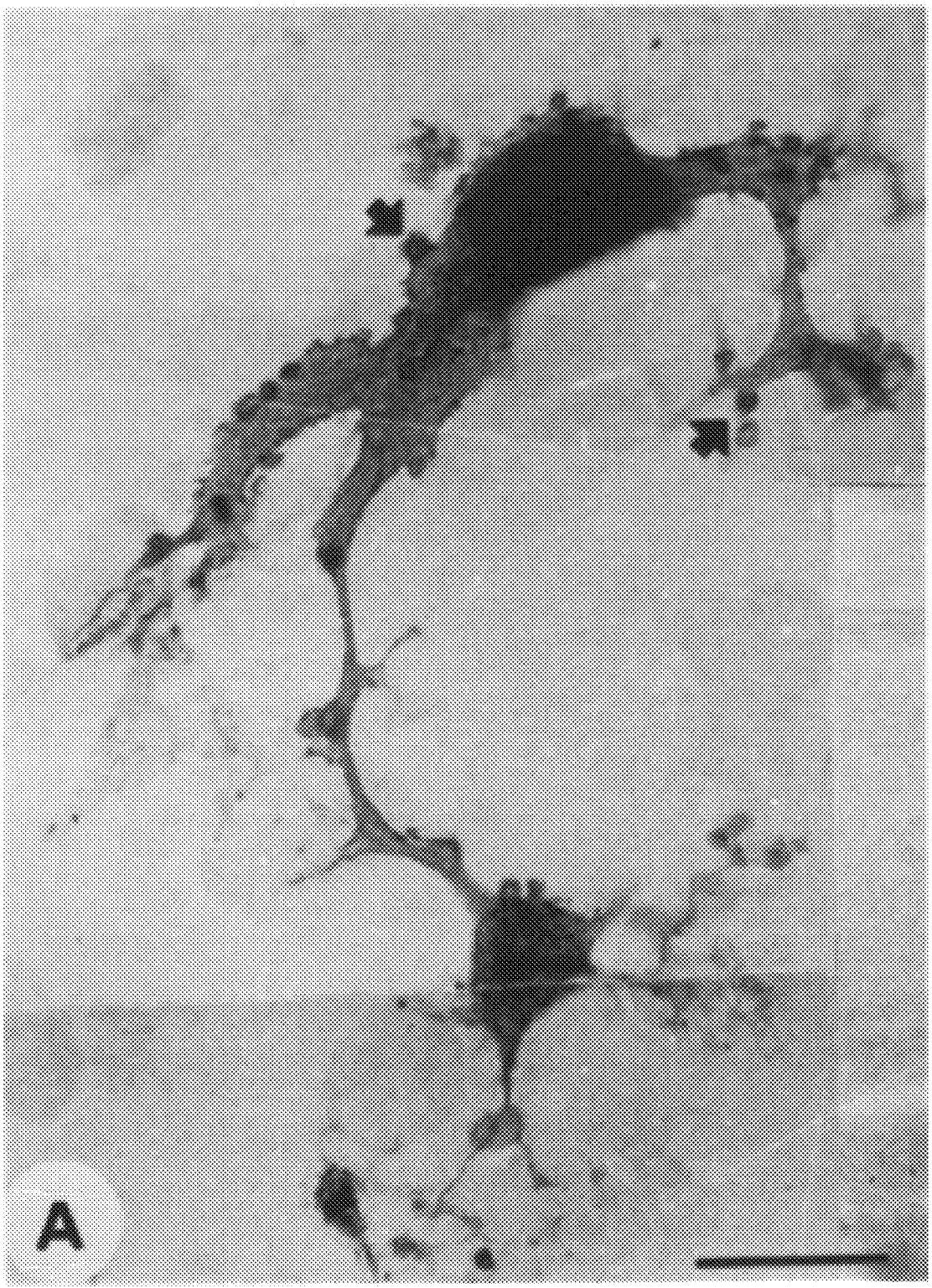
FIG. 4. (Panels A–C) Examples of varicosities on B-50/GAP-43-expressing Vero cells and ultrastructural localization of B-50/GAP-43 48 hours following infection with dvHCB-50. In some Vero cells high local concentrations of B-50/GAP-43 (arrows) are observed at the plasma membrane of cellular processes. Note that these foci of high B-50 expression are often associated with varicosities. The Scale Bar is 19 μm.
Figure 4A:
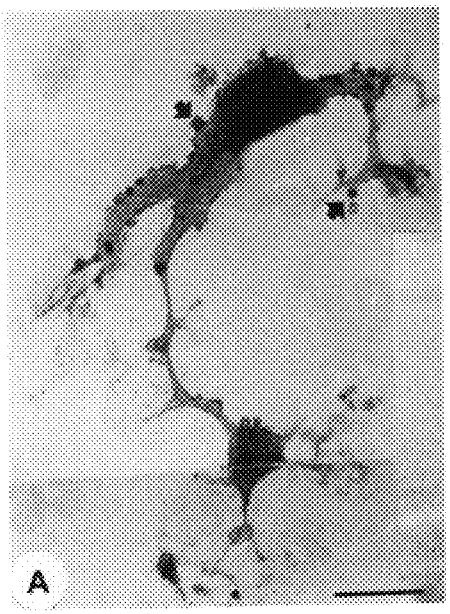
Figure 4B:
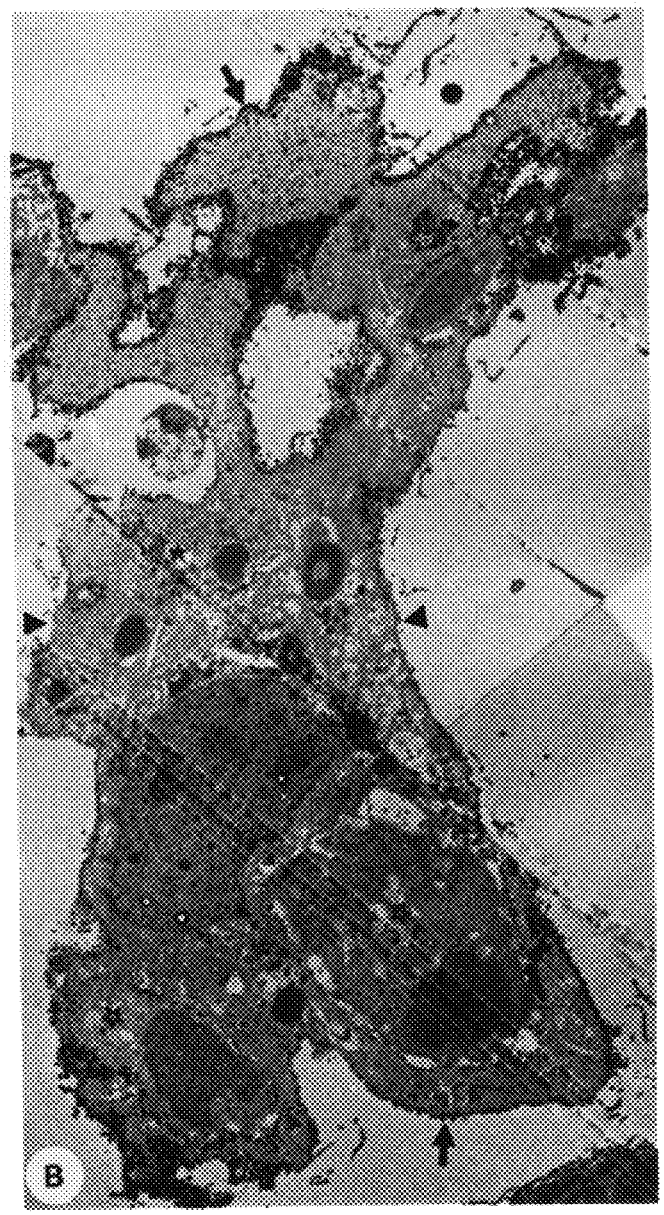
Figure 4C:
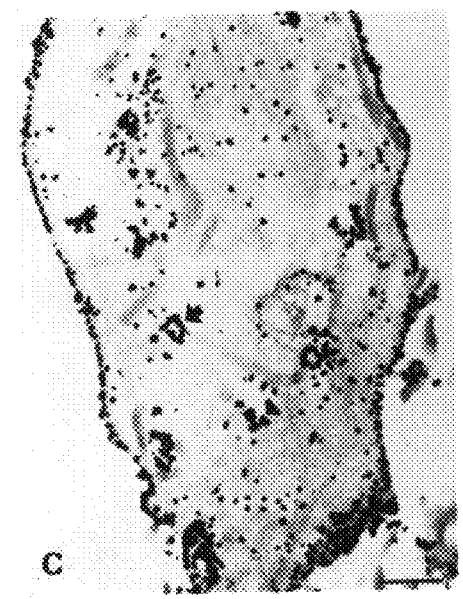
Figure 5A:
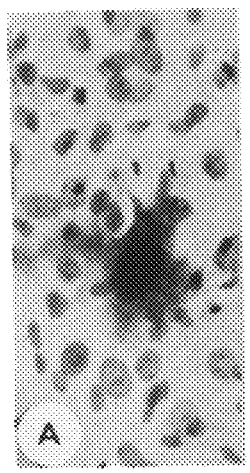
FIG. 5 (Panels A–E). Changes in the shape of rabbit skin cells expressing B-50/GAP-43. Rabbit skin cells expressed either β-gal (A,B) or B-50/GAP-43 (C,D,E) 48 hours after infection with dvHCL or dvHCB-50, respectively. Note the changes in cell shape in rabbit skin cells expressing B-50/GAP-43. (E) is a detail of the cell in (D) and illustrates multiple processes terminating in growth cone like structures. The scale bar is 50 μm for panels A,B,C,D and 19 μm for panel E.
Figure 5B:
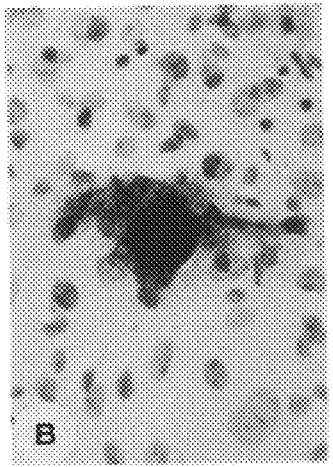
Figure 5C:
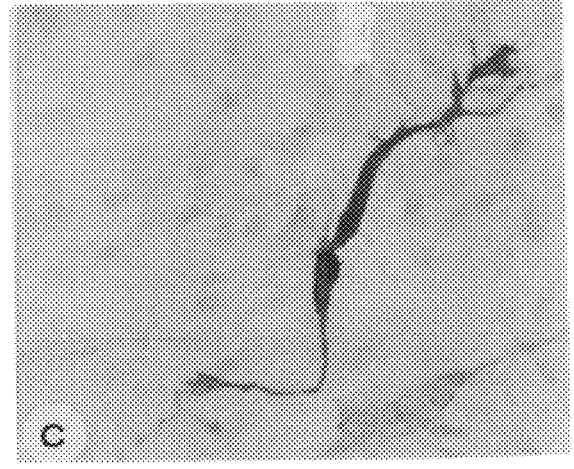
Figure 5D:
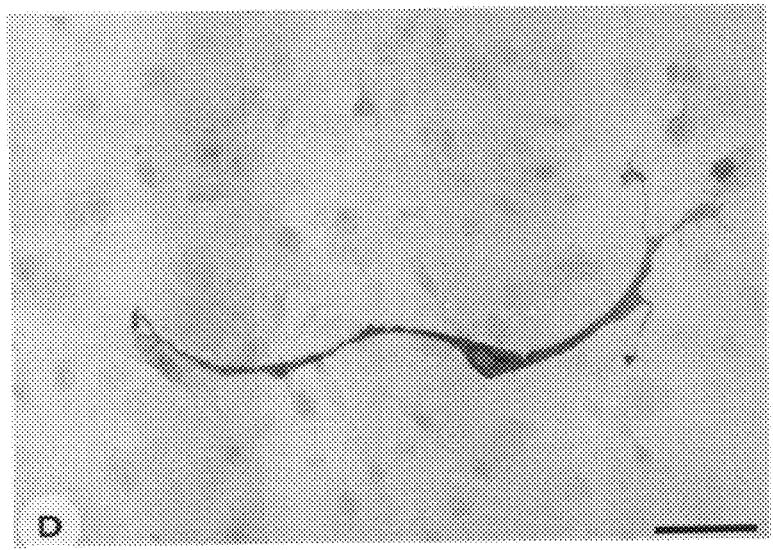
Figure 5E:
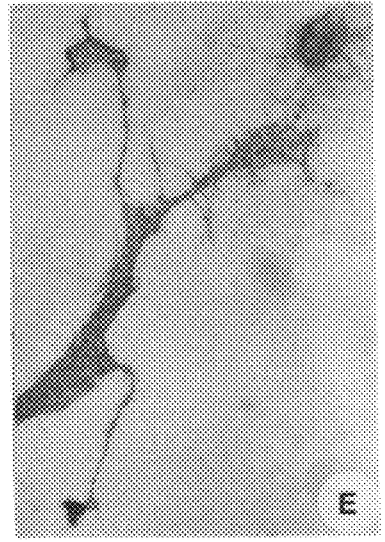

Effect of B-50/GAP-43 on the morphology of non-neuronal cells. Vero cells at a culture density of $2 \times 10^4$ cells/cm$^2$ (covering approximately 20% of the microscope slide) were infected with dvHCB-50 or with dvHCL and their morphology was studied at 6, 10, 24, 48 and 72 hours post-infection. Visual inspection of dvHCB-50 infected Vero cells revealed the occurrence of striking changes in the morphology of the B-50/GAP-43 immunoreactive cells in a time dependent fashion. Such changes were not observed in the β-gal positive cells (FIG. 3). At 10 hours after infection, B-50/GAP-43 positive cells were significantly larger in size than the β-gal cells. At this time point most B-50/GAP-43 positive cells exhibited irregular membranes but no long processes were observed. At 24, 48 and 72 hours post-infection, two distinct phenotypes were apparent (FIG. 3): (1) virtually all B-50/GAP-43 cells were larger in size than the cells expressing β-gal and exhibited ruffled membranes and filopodial-like extensions; (2) a second class of cells exhibited additional long processes (a process is defined as an extension longer than 15 μm), often terminating in club-shaped growth cone-like structures. First order processes emanating directly from the cell surface occasionally branched to form second order extensions (FIG. 3D,F,G). In both phenotypes swellings along the plasma membrane resembling varicosities were present usually containing high levels of B-50/GAP-43 (FIG. 4). The morphological changes in B-50/GAP-43 expressing Vero cells were seen in 4 independent experiments. In addition, similar changes in cell shape were observed in another non-neuronal cell line, the rabbit skin cells. The changes in these cells were only investigated at 48 hours after infection but were comparable to the effects seen in the Vero cells (FIG. 5).

Ultrastructural studies showed that B-50/GAP-43 was predominantly localized at the plasma membrane of the processes formed by the Vero cells. Some immunolabelling was associated with vesicular structures that appeared to be in-transit in the processes (FIG. 4). Immunolabelled processes were often in intimate contact with non-labelled cells and appeared to prefer their surface as a matrix for extension of their processes.

Figure 6B:
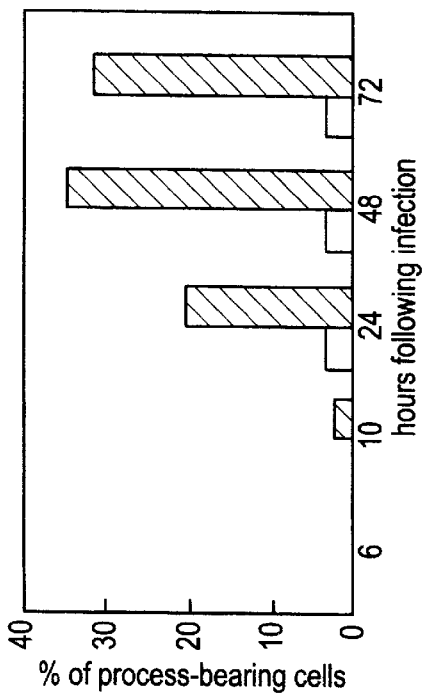
FIG. 6 (Panels A–D). Quantitation of dvHCL and dvHCB-50 infected vero cells at various times following infection. Vero cells cultured on poly-L-lysine coated microscope slides were infected with dvHCL or dvHCB-50. Cells were fixed at 6, 10, 24, 48 and 72 hours following infection and β-gal and B-50/GAP-43 positive cells were identified with a histochemical staining (β-gal) or immunocytochemically (B-50/GAP-43) as detailed in the methods section. The cell surface area (A), the percentage of process-bearing cells (B), the mean number of processes per process-bearing cell (C) and the mean length of individual processes were determined using a computerized image analyzer at 6, 10, 24, 48 and 72 hours following infection with dvHCL (black bars) and dvHCB-50 (grey bars). The numbers of cells analyzed at each time point is indicated in the bars of panel A. Statistical analysis of the results was performed with a student's t-test (*p<0.05 dvHCL infected cells versus dvHCB-50 infected cells).
Figure 6D:
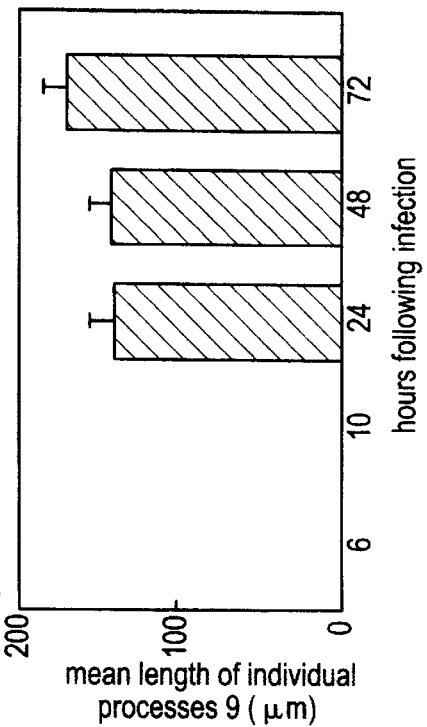
Figure 6A:
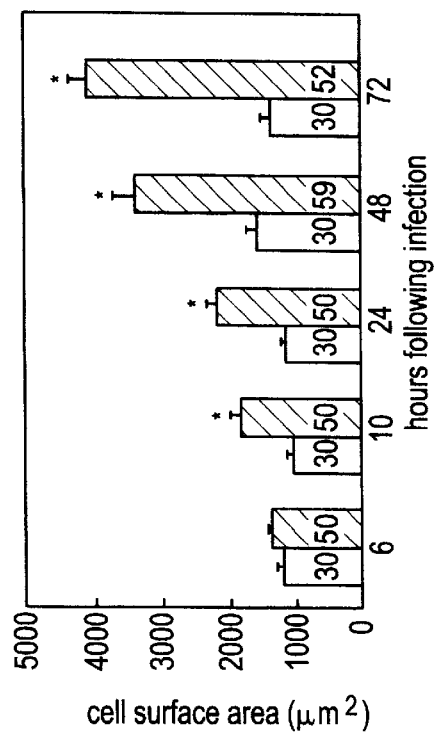
Figure 6C:
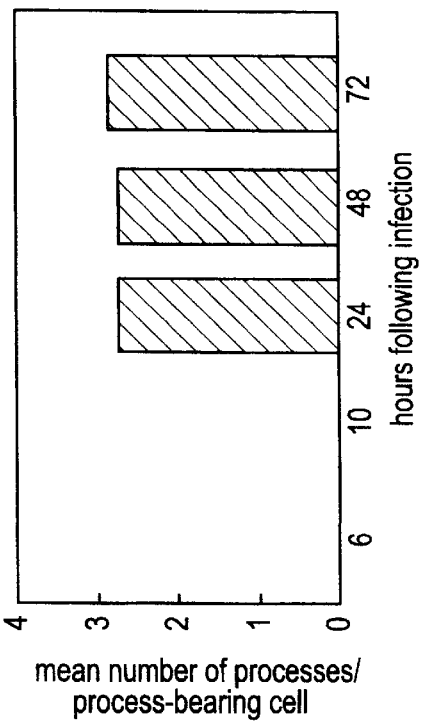

Quantitative analysis of B-50/GAP-43-induced morphological changes. The changes in the shape of Vero cells were further analyzed with an image analyzer. The cell surface area, the number of cells with one or more processes, the length of individual processes and the number of processes per process-bearing cell of 30 to 59 cells at each time point were recorded (FIG. 6). The surface area of the B-50 positive cells increased gradually from 10 hours up to 72 hours post-infection (FIG. 6A). At 72 hours the B-50 positive cells were 3.0 times larger in size than the β-gal expressing cells. B-50 positive cells with processes were not observed at 6 hours but started to appear between 10 and 24 hr post-infection. At 72 hours, 31% of the cells exhibited processes with a mean length of 165±14.5 μm (FIG. 6B,C). The mean number of processes per process-bearing cell increased sharply from virtually no processes at 10 hours following infection to 2.7 processes per cell at 24 hours following infection. The mean number of processes per process-bearing cell was stable between 24 and 72 hours post-infection (FIG. 6D). This quantitative analysis of Vero cells shows that the B-50/GAP-43 positive cells become more complex over time and retain their changed morphology in culture for at least 72 hours.

Discussion

The present example demonstrates preparation of a defective HSV vector containing the B-50/GAP-43 gene. These vectors transfer and express the B-50/GAP-43 gene in cells in tissue culture. B-50/GAP-43 expression in non-neuronal cells induces progressive changes in the shape of these cells eventually resulting in a considerable number of cells with a neuron-like morphology. This demonstrates that B-50/GAP-43 can initiate changes in cell shape and suggests a direct involvement of this growth-associated protein in the elaboration of cellular processes. These results also have implications for the maintenance of cells in tissue culture, since expression of B-50/GAP-43 resulted in robust behavior of even non-neuronal cells.

These results differ in two important aspects from previously reported B-50/GAP-43 induced changes in cell shape (Zuber et al., 1989, Science 244:1193–1195; Widmer and Caroni, 1993, J. Cell Biol. 120:503–512). First, the previous changes were quite modest as compared to the data presented here. For instance transfection of a B-50/GAP-43 expression vector in COS cells increased their cell surface area from 1000 μm$^2$ to 1340 μm$^2$ (Widmer and Caroni, 1993, supra) whereas the surface area of the Vero cells infected with the pHCB-50 vector increased from 1342 μm$^2$ to 4044 m$^2$. Stably transfected CHO cell lines exhibited membrane ruffling and filopodial extensions of 20 μm to 75 μm in only 15% to 40% of the cells (Zuber et al., 1989, supra), whereas virtually all cells expressing B-50/GAP-43 undergo cell surface changes. In addition, one third of these cells express processes with a mean length of 165 μm. This is more than twice as long as the filopodial extensions seen on CHO cells.

A second important difference between the previous cellular response to B-50/GAP-43 expression and the present results is in the timing of the changes. The previous morphological effects manifested in the first 2 to 4 hours following plating of the cells and were of a highly transient nature. In contrast in cells expressing B-50/GAP-43 via a defective HSV vector the cellular morphology gradually becomes more complex and the induced changes persisted up to 72 hours in culture. Although the differences in the results in Vero and rabbit skin cells and those seen in CHO and COS cells may be partially related to the changes in cell type used, this is only a formal possibility. COS cells are derived from CV-1 cells. CV-1 cells and Vero cells are both derived from African green monkey kidney cells. Thus, COS cells and Vero cells are closely related cell types.

Although no attempt was made to quantify the amount of B-50/GAP-43 production in individual cells in culture, the polyclonal antibody used in this study was used at a much higher dilution (1/2500) than usual in light microscope studies on B-50 in brain sections (1/1000). At this higher dilution, most of the cells were darkly stained indicating a high level of B-50 synthesis. The use of a strong viral promoter to drive gene expression, and transfer of the gene via a defective viral vector may have contributed to this high level expression of B-50/GAP-43. There are a number of explanations for these observations. The CMV IE promoter is a very strong transcriptional activator (Scharfmann et al., 1991, Proc. Natl. Acad. Sci. U.S.A. 88:4626–4630). Furthermore, each vector packages numerous copies of the plasmid genome—up to 150 kb (Spaete and Frenkel, 1982, Cell 30:295–304). Each infected cell therefore is expected to contain numerous copies of the B-50/GAP-43 transcription unit, as opposed to a single copy in a stable cell line. Finally, gene transfer through viral infection results in greater uniformity of gene delivery than with transfection of naked DNA, in which the number of copies of a gene entering a cell can be quite variable. The defective HSV vector permits uniform gene transfer, which is one reason for creating a stably transfected cell line, and the vector also transfers the multiple copies in an episomal form, thereby limiting the possibility of low gene expression due to insertional influences on a single copy gene. Thus, the dramatic and persistent cell surface morphological changes in virtually the total population of B-50/GAP-43 expressing cells may be related to the high level of expression that can be achieved by defective herpes viral vector gene transfer.

EXAMPLE 2

An adenovirus vector and an adeno-associated virus vector containing the B-50/GAP-43 gene have been prepared. Also, an AAV vector containing the lacZ gene has been prepared as a model to demonstrate that the AAV vector can transfect neural cells.

Figure 7:
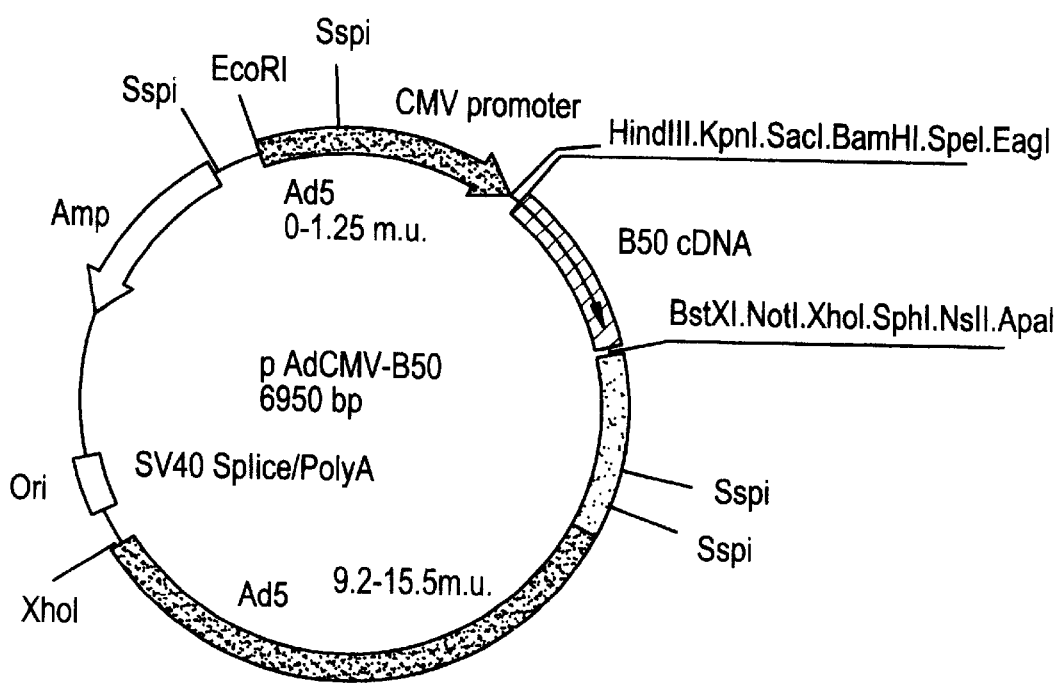
FIG. 7. Diagram of pAdCMV-B50 plasmid. This plasmid contains the B-50/GAP-43 coding sequence under control of the CMV promoter, which was cut out of the pHCB-50 amplicon, for expression in an adenovirus vector. The SV40 polyadenylation signal was used in this plasmid as well.
Figure 8:
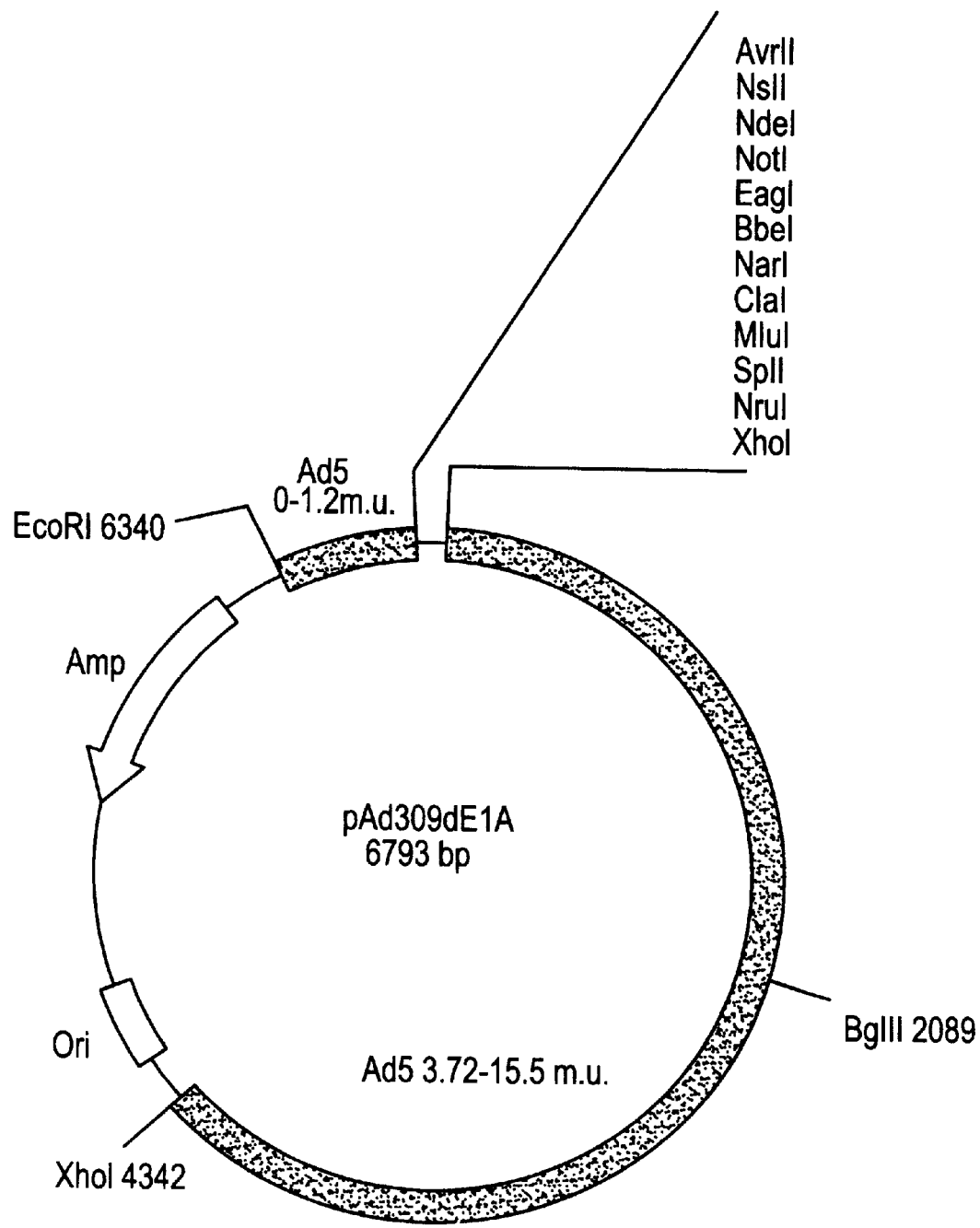
FIG. 8. Diagram of pAd309dE1A plasmid, on which pAdCMV-B50 is based. This plasmid was prepared from plasmid pAd309SholC (Shenk) and pSL301.

Protocol for generating GAP-43/B-50 adenoviral vector. Plasmid pAdCMV-B-50, which contains the gene encoding B-50/GAP-43 under control of the CMV immediate early promoter, is shown in FIG. 7. This vector was prepared from plasmid pAd309XholC (FIG. 8), obtained form T. Shenk (Princeton University, Princeton, N.J.). This is a clone containing the extreme left end 5.5 kb of adenovirus type 5, strain 309 (referred to as dl309), inserted into plasmid pML, which is a derivative of pBR322. This is equivalent to 15.5 map units (m.u.), or 15.5% of adenovirus genome, which is approximately 36 kb total in size. Clone pAdCMV-B50 was generated by digesting pAd309dE1A with ClaI/BglII. Plasmid pHCMV-B50 (FIG. 1) was cut with Cla/Xba to isolate the CMV/B-50 portion. pHCMV-B50 was also cut with Xba/BamH1 to isolate the SV40 polyA signal site. pAdCMV-B50 was then generated by three fragment ligation.

Adenovirus dl309 was grown on 293 cells (from ATCC), which constitutively express the adenoviral E1a protein. To generate dl309 DNA, virus was isolated by freeze/thaw cycles, and then virions were purified by banding twice on a cesium chloride step gradient. Purified virions were precipitated with ethanol, resuspended in PBS, and then virions were lysed with 200 μg/ml Proteinase K, 1% SDS, 5 mM EDTA at 37° C. for 2 hours. Lysate was extracted twice with phenol/chloroform, followed by chloroform extraction, and then the supernatant with DNA was ethanol precipitated in order to isolate DNA.

Viral DNA was then digested with XbaI to remove the extreme left end (approximately 900 bp, which includes the adenoviral packaging signal and E1a. region), and the large 35 kb fragment was purified on a sucrose step gradient. Plasmid pAdCMV-B50 was linearized with EcoR1, which is at the end of the Ad5 sequence within the plasmid. Linearized plasmid and dl309 large (3 kb) fragment were co-transfected into 293 cells. The absence of a packaging signal prevents packaging of the 35 kb dl309 fragment. The presence of this signal in the Ad5 sequence flanking the CMV-B50 in pAdCMV-B50 (0–1.25 m.u.) provides the selective pressure for recombination. The Ad5 9.2–15.5 m.u. region flanking the other side of CMV-B50 is the region of overlap with the dl309 35 kb fragment, which is where the recombination occurs. The result was Ad309CMV-B-50, in which the CMV-B50 gene replaces the 1.25–9.2 m.u. region of dl309. This region includes the E1a gene, without which adenovirus is incapable of replication. The recombinant vector replicates on 293 cells, however, since they constitutively express E1a. Viral plaques were identified approximately 1 week following transfection. Plaques were picked with a pasteur pipette, placed in buffer, and left in the refrigerator overnight. The next day, a small aliquot was removed, boiled and then subjected to the polymerase chain reaction (PCR), using primers specific for the B-50/GAP-43 gene, thereby identifying recombinant viruses containing the CMV-B50 transcription unit. These vectors were then grown to high titer on fresh 293 cells prior to use.

Protocol for generating pAAVlac.26 and pAAV-CMV-B-50. Plasmids SSV9 and Ad8 were obtained from Richard Jude Samulski (University of Pittsburgh, Pittsburgh, Pa. ). SSV9 is a clone containing the entire adeno-associated virus (AAV) genome inserted into the PvuII site of plasmid pEMBL. This clone also contains two XbaI sites adjacent to the end of the AAV termini which contain AAV replication and packaging (i.e., recognition) signals. Cleavage with XbaI therefore removes the majority of the AAV genome (4.1 kb), leaving two 180 bp fragments of AAV termini at the ends of the linearized plasmid. This permits insertion of a transcription unit between the AAV termini, in order to create the AAV vector. Ad8 is a plasmid which contains the majority of the AAV genome (4.1 kb) without the flanking AAV termini. Therefore, this plasmid expresses AAV proteins necessary for viral replication, but is incapable of replication and packaging into virions due to the absence of termini. To package a vector derived by XbaI cleavage of SSV9, the vector is co-transfected into 293 cells with Ad8, which provides the proteins necessary to replicate and package the SSV9-derived vector into AAV virions. The next day, these cells are infected with adenovirus dl309, since expression of the AAV proteins and replication of the vector also requires proteins encoded by adenovirus (since wild-type AAV is a defective virus which grows only in the presence of adenovirus). The result is a mixed population, containing progeny dl309 and the SSV-9 derived vector packaged into AAV virions (Ad8 is not packaged and is lost). The SSV9-derived vector expresses no viral genes and contains only the desired foreign gene insert. Virus is isolated by multiple freeze/thaw cycles of harvested, infected cells. The residual progeny dl309 in the stock was eliminated by heating the stock to 56° C., which destroys adenovirus but does not harm AAV. A pure AAV stock may also be generated by banding the mixed stock on a cesium chloride gradient, since the difference in size between the adenovirus and AAV particles permit separation on a gradient.

Figure 9:
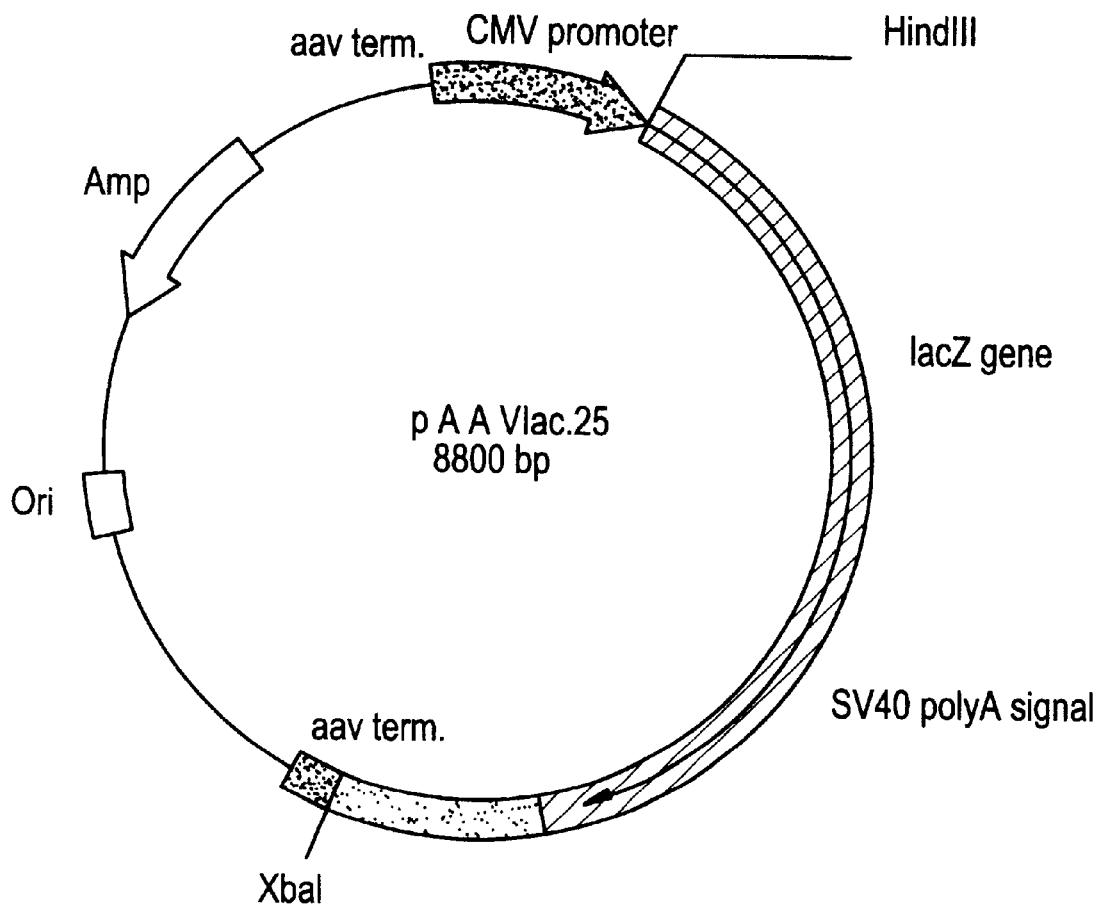
FIG. 9. Diagram of plasmid pAAVlac.26. This plasmid was prepared for expression in an adeno-associated virus (AAV) vector. The plasmid contains the lacZ gene under control of the CMV promoter, with the SV40 polyA signal at the 3' end. The diagram also indicates the position of the Ori site, the AAV terminii, and restriction endonuclease sites.
Figure 10:
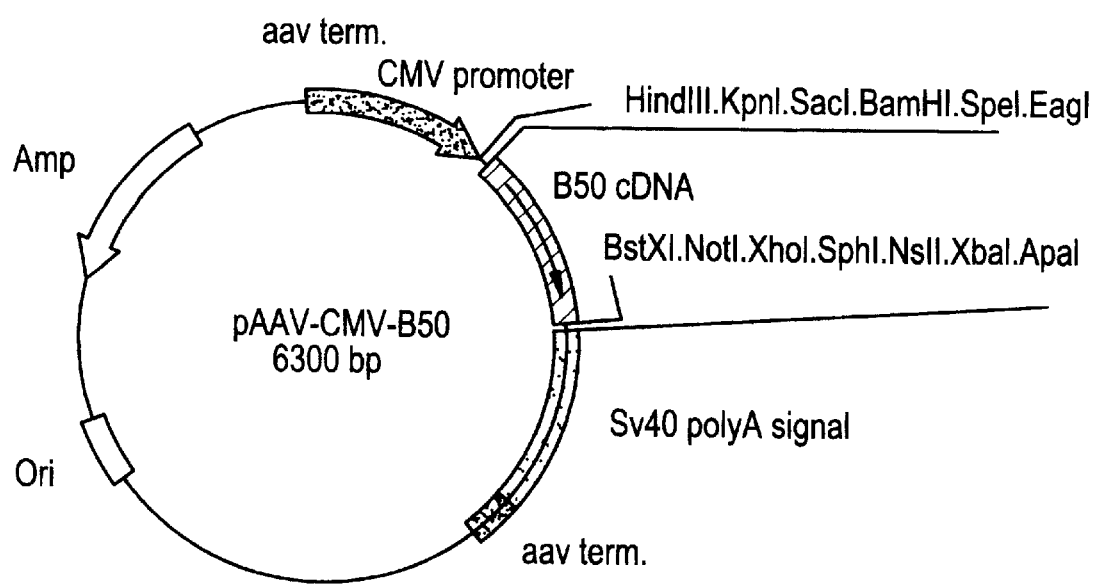
FIG. 10. Diagram of plasmid pAAV-CMV-B-50. This plasmid was prepared by digestion of the pAdCMV-B50 plasmid. This plasmid is designed for expression in an AAV vector.

Plasmid pAAVlac.26 (FIG. 9) was generated by digestion of pHCL (Kaplitt et al., 1991, Molec. Cell. Neurosci. 2:320–330) with SpeI/XbaI to liberate CMV-lacZ-SV40 polyA signal unit. This fragment was ligated into SSV9 digested with XbaI and treated with phosphatase.

Plasmid pAAV-CMV-B50 (FIG. 11) was generated as follows. pAdCMV-B50 was digested with Avril/XbaI to liberate a fragment with the CMV promoter and the B-50/GAP-43 gene lacking, however, an SV40 poly-A signal. This fragment was inserted between the AAV termini by ligation to SSV9 digested with XbaI. Avril and XbaI are compatible ends, but ligation destroys both recognition sites. Therefore, the resulting plasmid contained a single XbaI site at the 3' end of the B-50/GAP-43 gene. This site was digested with XbaI, and an SV40 poly A signal was inserted. This signal was isolated by XbaI digestion of pHCMV-B50. The resulting plasmid was called pAAV-CMV-B-50. Stocks of AAV vector containing CMV-B50 were then generated by co-transfecting this plasmid with Ad8 into 293 cells, followed by superinfection the next day with dl 309, as described above.

Expression of LacZ in Transfected Neurons in vivo. AAV vector containing pAAVlac.2was introduced into brain tissue as described in Kaplitt et al. (1991, supra). Tissues were removed, fixed and stained in accordance with X-Gal histochemical analysis as described. Blue staining in cells indicates transfection with and expression of the lacZ gene, which encodes β-galactosidase. The extent of transfection demonstrated in this experiment is quite satisfactory, particularly considering that AAV, which is not known as a neurotrophic virus, was the vector.

Comparison of the 3 different CMV-B50 vectors. The adenovirus vector is a recombinant vector, in that the CMV-B50 was inserted into the genome of the adenovirus, in place of a necessary viral gene, which is then provided in the cell in which the virus is grown. The AAV vector is a defective vector similar to the defective HSV vector, in that the AAV vector contains no viral genes and only contains and expresses the B-50/GAP-43 gene under the control of the CMV promoter. The vector is simply packaged into an AAV coat in the presence of proteins provided by the plasmid Ad8 and helper adenovirus. Unlike the defective HSV vector, however, the outside coat of the AAV vector comes from AAV proteins provided by Ad8, not from the adenovirus. The adenovirus is needed only for replication. With the defective HSV vector, a plasmid containing no viral genes but only the CMV-B50 is replicated and packaged into viral particles in the presence of proteins provided by a helper herpes virus, but the viral coat of the defective vector is composed of proteins from this helper herpes virus; there is no distinct type of defective HSV vector coat. So the AAV vector can be completely purified from the helper adenovirus in the stock by separation on cesium chloride gradients or heat-killing the adenovirus specifically, whereas the residual HSV in the defective HSV stock cannot be removed due to the similarity in the outer coats between helper and defective particles. Therefore, a mutant HSV must be used as a helper to prevent disease due to the residual helper virus which cannot be removed.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various references are cited throughout this specification, each of which is incorporated herein by reference in its entirety.

What is claimed is:

1. A method for providing short term, high level expression of B-50/GAP-43 in a neural tissue in a subject comprising introducing and expressing a vector containing a gene encoding B-50/GAP-43 operably associated with a promoter into the neural tissue of the subject, wherein the promoter controls the short term, high level expression of the B-50/GAP-43 gene; and wherein said short term, high level expression stimulates neuronal outgrowth in a nerve cell.

2. The method according to claim 1, wherein the vector is a viral vector.

3. The method according to claim 2, wherein the viral vector is selected from the group consisting of herpesvirus, adenovirus, and Epstein-Barr Virus.

4. The method according to claim 2 wherein the viral vector is a defective viral vector.

5. The method according to claim 4 wherein the viral vector is a herpesvirus.

6. The method according to claim 4 wherein the viral vector is an adenovirus.

7. The method according to claim 1 wherein the B-50/GAP-43 gene is a rat gene.

8. The method according to claim 1 wherein the promoter is the human cytomegalovirus immediate early promoter.

9. The method according to claim 1 wherein the promoter is an inducible promoter.

* * * * *